US011207110B2

(12) United States Patent
Pool et al.

(10) Patent No.: US 11,207,110 B2
(45) Date of Patent: *Dec. 28, 2021

(54) BONE GROWTH DEVICE AND METHOD

(71) Applicant: NuVasive Specialized Orthopedics, Inc.

(72) Inventors: Scott Pool, Laguna Hills, CA (US); Blair Walker, Mission Viejo, CA (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/529,692

(22) Filed: Aug. 1, 2019

(65) Prior Publication Data
US 2019/0350627 A1 Nov. 21, 2019

Related U.S. Application Data

(60) Continuation of application No. 13/892,182, filed on May 10, 2013, now abandoned, which is a division of
(Continued)

(51) Int. Cl.
*A61B 17/66* (2006.01)
*A61B 17/72* (2006.01)
(Continued)

(52) U.S. Cl.
CPC ...... *A61B 17/7216* (2013.01); *A61B 17/1725* (2013.01); *A61B 17/66* (2013.01);
(Continued)

(58) Field of Classification Search
CPC ............ A61B 17/7216; A61B 17/7225; A61B 17/7014; A61B 17/7016; A61B 17/7017
See application file for complete search history.

(56) References Cited

U.S. PATENT DOCUMENTS 2,702,031 A 2/1955 Wenger
3,111,945 A 11/1963 Von Solbrig
(Continued)

FOREIGN PATENT DOCUMENTS

CA 2655093 12/2007
CN 1697630 A 11/2005
(Continued)

OTHER PUBLICATIONS

White, III et al., "The clinical biomechanics of scoliosis.", Clinical Orthopaedics and Related Research, 1976, pp. 100-112, 118.
(Continued)

*Primary Examiner* — Jan Christopher L Merene
(74) *Attorney, Agent, or Firm* — Hoffman Warnick LLC

(57) ABSTRACT

An intramedullary lengthening device includes a housing and a distraction shaft. The intramedullary lengthening device is placed within a cavity of two bone sections (either already separated or purposely separated for insertion of the device). The distraction shaft of the intramedullary lengthening device is attached to the one of the bone sections using, for example, one or more attachment screws. The housing of the intramedullary lengthening device is attached to the second bone section using, for instance, one or more attachment screws. Over the treatment period, the bone is continually distracted, creating a new separation into which osteogenesis can occur. In one embodiment, the intramedullary lengthening device includes an actuator and an extension rod, which can be attached to one other.

16 Claims, 17 Drawing Sheets

Related U.S. Application Data application No. 12/875,585, filed on Sep. 3, 2010, now Pat. No. 8,449,543.

(60) Provisional application No. 61/363,986, filed on Jul. 13, 2010, provisional application No. 61/240,071, filed on Sep. 4, 2009.

(51) Int. Cl.
  *A61B 17/17* (2006.01)
  *A61B 17/88* (2006.01)
  *A61B 17/68* (2006.01)

(52) U.S. Cl.
  CPC ....... *A61B 17/8875* (2013.01); *A61B 17/8888* (2013.01); *A61B 2017/681* (2013.01)

(56) References Cited

U.S. PATENT DOCUMENTS

| | | |
|---|---|---|
| 3,333,333 A | 8/1967 | Noack |
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,810,259 A | 5/1974 | Summers |
| 3,817,237 A | 6/1974 | Bolduc |
| 3,892,182 A | 7/1975 | Covarrubias et al. |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland |
| 4,056,743 A | 11/1977 | Clifford |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher |
| 4,386,603 A | 6/1983 | Mayfield |
| 4,448,191 A | 5/1984 | Rodnyansky |
| 4,486,176 A | 12/1984 | Tardieu |
| 4,501,266 A | 2/1985 | McDaniel |
| 4,522,501 A | 6/1985 | Shannon |
| 4,537,520 A | 8/1985 | Ochiai |
| 4,550,279 A | 10/1985 | Klein |
| 4,561,798 A | 12/1985 | Elcrin |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich |
| 4,700,091 A | 10/1987 | Wuthrich |
| 4,731,051 A | 3/1988 | Fischell |
| 4,747,832 A | 5/1988 | Buffet |
| 4,776,330 A | 10/1988 | Chapman et al. |
| 4,854,304 A | 8/1989 | Zielke |
| 4,904,861 A | 2/1990 | Epstein |
| 4,931,055 A | 6/1990 | Bumpus |
| 4,940,467 A | 7/1990 | Tronzo |
| 4,957,495 A | 9/1990 | Kluger |
| 4,973,331 A | 11/1990 | Pursley |
| 5,010,879 A | 4/1991 | Moriya |
| 5,030,235 A | 7/1991 | Campbell, Jr. |
| 5,041,112 A | 8/1991 | Mingozzi |
| 5,064,004 A | 11/1991 | Lundell |
| 5,074,882 A | 12/1991 | Grammont et al. |
| 5,092,889 A | 3/1992 | Campbell, Jr. |
| 5,098,435 A | 3/1992 | Stednitz et al. |
| 5,116,378 A | 5/1992 | Carbone |
| 5,122,141 A | 6/1992 | Simpson et al. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders |
| 5,306,275 A | 4/1994 | Bryan |
| 5,326,360 A | 7/1994 | Kotz |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson |
| 5,466,261 A | 11/1995 | Richelsoph |
| 5,468,030 A | 11/1995 | Walling |
| 5,480,437 A | 1/1996 | Draenert |
| 5,505,733 A | 4/1996 | Justin et al. |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Ten Eyck et al. |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,640,847 A | 6/1997 | Nakajima et al. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo |
| 5,830,221 A | 11/1998 | Stein et al. |
| 5,879,375 A | 3/1999 | Larson, Jr. |
| 5,902,304 A | 5/1999 | Walker |
| 5,935,127 A | 8/1999 | Border |
| 5,945,762 A | 8/1999 | Chen |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva |
| 6,162,223 A | 12/2000 | Orsak |
| 6,183,476 B1 | 2/2001 | Gerhardt |
| 6,200,317 B1 | 3/2001 | Aalsma et al. |
| 6,234,956 B1 | 5/2001 | He et al. |
| 6,237,956 B1 | 5/2001 | Haba et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei |
| 6,331,744 B1 | 12/2001 | Chen |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans |
| 6,416,516 B1 | 7/2002 | Stauch et al. |
| 6,417,750 B1 | 7/2002 | Sohn |

(56) References Cited

U.S. PATENT DOCUMENTS

| | | |
|---|---|---|
| 6,499,907 B1 | 12/2002 | Baur |
| 6,500,110 B1 | 12/2002 | Davey |
| 6,508,820 B2 | 1/2003 | Bales |
| 6,510,345 B1 | 1/2003 | Van Bentem |
| 6,537,196 B1 | 3/2003 | Creighton, IV |
| 6,554,831 B1 | 4/2003 | Rivard |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes |
| 6,616,669 B2 | 9/2003 | Ogilvie |
| 6,626,917 B1 | 9/2003 | Craig |
| 6,656,135 B2 | 12/2003 | Zogbi |
| 6,656,194 B1 | 12/2003 | Gannoe |
| 6,667,725 B1 | 12/2003 | Simons |
| 6,673,079 B1 | 1/2004 | Kane |
| 6,702,816 B2 | 3/2004 | Buehler |
| 6,706,042 B2 | 3/2004 | Taylor |
| 6,709,293 B2 | 3/2004 | Mori |
| 6,730,087 B1 | 5/2004 | Butsch |
| 6,761,503 B2 | 7/2004 | Breese |
| 6,769,499 B2 | 8/2004 | Cargill |
| 6,789,442 B2 | 9/2004 | Foerch |
| 6,796,984 B2 | 9/2004 | Soubeiran |
| 6,802,844 B2 | 10/2004 | Ferree |
| 6,809,434 B1 | 10/2004 | Duncan |
| 6,835,207 B2 | 12/2004 | Zacouto et al. |
| 6,849,076 B2 | 2/2005 | Blunn et al. |
| 6,852,113 B2 | 2/2005 | Nathanson |
| 6,918,838 B2 | 7/2005 | Schwaerzler |
| 6,918,910 B2 | 7/2005 | Smith et al. |
| 6,921,400 B2 | 7/2005 | Sohngen |
| 6,923,951 B2 | 8/2005 | Contag |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler |
| 7,105,968 B2 | 9/2006 | Nissen |
| 7,114,501 B2 | 10/2006 | Johnson |
| 7,115,129 B2 | 10/2006 | Heggeness |
| 7,135,022 B2 | 11/2006 | Kosashvili |
| 7,160,312 B2 | 1/2007 | Saadat |
| 7,163,538 B2 | 1/2007 | Altarac |
| 7,189,005 B2 | 3/2007 | Ward |
| 7,191,007 B2 | 3/2007 | Desai |
| 7,218,232 B2 | 5/2007 | Disilvestro |
| 7,238,191 B2 | 7/2007 | Bachmann |
| 7,241,300 B2 | 7/2007 | Sharkawy |
| 7,243,719 B2 | 7/2007 | Baron |
| 7,255,682 B1 | 8/2007 | Bartol, Jr. |
| 7,282,023 B2 | 10/2007 | Frering |
| 7,285,087 B2 | 10/2007 | Moaddeb |
| 7,302,015 B2 | 11/2007 | Kim |
| 7,302,858 B2 | 12/2007 | Walsh |
| 7,314,443 B2 | 1/2008 | Jordan |
| 7,333,013 B2 | 2/2008 | Berger |
| 7,357,037 B2 | 4/2008 | Hnat |
| 7,357,635 B2 | 4/2008 | Belfor et al. |
| 7,360,542 B2 | 4/2008 | Nelson |
| 7,390,007 B2 | 6/2008 | Helms |
| 7,390,294 B2 | 6/2008 | Hassler, Jr. |
| 7,402,134 B2 | 7/2008 | Moaddeb |
| 7,402,176 B2 | 7/2008 | Malek |
| 7,429,259 B2 | 9/2008 | Cadeddu |
| 7,445,010 B2 | 11/2008 | Kugler |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt |
| 7,561,916 B2 | 7/2009 | Hunt |
| 7,584,788 B2 | 9/2009 | Baron et al. |
| 7,601,156 B2 | 10/2009 | Robinson |
| 7,611,526 B2 | 11/2009 | Carl et al. |
| 7,618,435 B2 | 11/2009 | Opolski |
| 7,658,754 B2 | 2/2010 | Zhang |
| 7,666,184 B2 | 2/2010 | Stauch |
| 7,666,210 B2 | 2/2010 | Franck |
| 7,678,136 B2 | 3/2010 | Doubler |
| 7,678,139 B2 | 3/2010 | Garamszegi |
| 7,708,737 B2 | 5/2010 | Kraft |
| 7,708,762 B2 | 5/2010 | McCarthy |
| 7,727,143 B2 | 6/2010 | Birk |
| 7,753,913 B2 | 7/2010 | Szakelyhidi, Jr. |
| 7,753,915 B1 | 7/2010 | Eksler et al. |
| 7,762,998 B2 | 7/2010 | Birk |
| 7,763,080 B2 | 7/2010 | Southworth |
| 7,766,855 B2 | 8/2010 | Miethke |
| 7,775,215 B2 | 8/2010 | Hassler, Jr. |
| 7,776,068 B2 | 8/2010 | Ainsworth |
| 7,776,075 B2 | 8/2010 | Bruneau |
| 7,776,091 B2 | 8/2010 | Mastrorio et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson |
| 7,837,691 B2 | 11/2010 | Cordes |
| 7,862,586 B2 | 1/2011 | Malek |
| 7,867,235 B2 | 1/2011 | Fell et al. |
| 7,875,033 B2 | 1/2011 | Richter |
| 7,887,566 B2 | 2/2011 | Hynes |
| 7,901,381 B2 | 3/2011 | Birk |
| 7,909,852 B2 | 3/2011 | Boomer |
| 7,918,844 B2 | 4/2011 | Byrum |
| 7,938,841 B2 | 5/2011 | Sharkawy |
| 7,985,256 B2 | 7/2011 | Grotz |
| 7,988,709 B2 | 8/2011 | Clark |
| 8,002,809 B2 | 8/2011 | Baynham |
| 8,011,308 B2 | 9/2011 | Picchio |
| 8,011,808 B2 | 9/2011 | Liu |
| 8,034,080 B2 | 10/2011 | Malandain |
| 8,043,299 B2 | 10/2011 | Conway |
| 8,043,338 B2 | 10/2011 | Dant |
| 8,057,472 B2 | 11/2011 | Walker et al. |
| 8,057,473 B2 | 11/2011 | Orsak |
| 8,057,513 B2 | 11/2011 | Kohm |
| 8,083,741 B2 | 12/2011 | Morgan |
| 8,092,499 B1 | 1/2012 | Roth |
| 8,095,317 B2 | 1/2012 | Ekseth |
| 8,105,360 B1 | 1/2012 | Connor |
| 8,105,363 B2 | 1/2012 | Fielding |
| 8,114,158 B2 | 2/2012 | Carl |
| 8,123,805 B2 | 2/2012 | Makower |
| 8,133,280 B2 | 3/2012 | Voellmicke |
| 8,147,517 B2 | 4/2012 | Trieu et al. |
| 8,147,549 B2 | 4/2012 | Metcalf, Jr. et al. |
| 8,162,897 B2 | 4/2012 | Byrum |
| 8,162,979 B2 | 4/2012 | Sachs |
| 8,177,789 B2 | 5/2012 | Magill et al. |
| 8,197,490 B2 | 6/2012 | Pool |
| 8,211,149 B2 | 7/2012 | Justis |
| 8,211,151 B2 | 7/2012 | Schwab |
| 8,211,179 B2 | 7/2012 | Molz, IV et al. |
| 8,216,275 B2 | 7/2012 | Fielding |
| 8,221,420 B2 | 7/2012 | Keller |
| 8,226,690 B2 | 7/2012 | Altarac |
| 8,236,002 B2 | 8/2012 | Fortin et al. |
| 8,241,331 B2 | 8/2012 | Arnin |
| 8,246,630 B2 | 8/2012 | Manzi |
| 8,252,063 B2 | 8/2012 | Stauch |
| 8,267,969 B2 | 9/2012 | Altarac |
| 8,278,941 B2 | 10/2012 | Kroh |
| 8,282,671 B2 | 10/2012 | Connor |
| 8,298,240 B2 | 10/2012 | Giger et al. |
| 8,323,290 B2 | 12/2012 | Metzger |
| 8,357,182 B2 | 1/2013 | Seme |
| 8,366,628 B2 | 2/2013 | Denker |

(56) References Cited

U.S. PATENT DOCUMENTS

| | | |
|---|---|---|
| 8,372,078 B2 | 2/2013 | Collazo |
| 8,386,018 B2 | 2/2013 | Stauch |
| 8,394,124 B2 | 3/2013 | Biyani |
| 8,403,958 B2 | 3/2013 | Schwab |
| 8,414,584 B2 | 4/2013 | Brigido |
| 8,419,801 B2 | 4/2013 | DiSilvestro et al. |
| 8,425,608 B2 | 4/2013 | Dewey |
| 8,435,268 B2 | 5/2013 | Thompson |
| 8,439,915 B2 | 5/2013 | Harrison et al. |
| 8,439,926 B2 | 5/2013 | Bojarski |
| 8,444,693 B2 | 5/2013 | Reiley |
| 8,449,543 B2 | 5/2013 | Pool |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria |
| 8,486,110 B2 | 7/2013 | Fielding et al. |
| 8,486,147 B2 | 7/2013 | De Villiers |
| 8,494,805 B2 | 7/2013 | Roche |
| 8,496,662 B2 | 7/2013 | Novak |
| 8,518,062 B2 | 8/2013 | Cole |
| 8,523,866 B2 | 9/2013 | Sidebotham |
| 8,529,474 B2 | 9/2013 | Gupta |
| 8,529,606 B2 | 9/2013 | Alamin et al. |
| 8,529,607 B2 | 9/2013 | Alamin |
| 8,556,901 B2 | 10/2013 | Anthony |
| 8,556,911 B2 | 10/2013 | Mehta |
| 8,556,975 B2 | 10/2013 | Ciupik |
| 8,562,653 B2 | 10/2013 | Alamin et al. |
| 8,568,457 B2 | 10/2013 | Hunziker |
| 8,579,979 B2 | 11/2013 | Edie |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann |
| 8,613,758 B2 | 12/2013 | Linares |
| 8,617,220 B2 | 12/2013 | Skaggs |
| 8,623,036 B2 | 1/2014 | Harrison |
| 8,632,544 B2 | 1/2014 | Haaja et al. |
| 8,632,548 B2 | 1/2014 | Soubeiran |
| 8,632,563 B2 | 1/2014 | Nagase |
| 8,636,771 B2 | 1/2014 | Butler |
| 8,636,802 B2 | 1/2014 | Serhan |
| 8,641,719 B2 | 2/2014 | Gephart |
| 8,641,723 B2 | 2/2014 | Connor |
| 8,657,856 B2 | 2/2014 | Gephart |
| 8,663,285 B2 | 3/2014 | Dall et al. |
| 8,663,287 B2 | 3/2014 | Butler |
| 8,668,719 B2 | 3/2014 | Alamin |
| 8,709,090 B2 | 4/2014 | Makower |
| 8,758,347 B2 | 6/2014 | Weiner |
| 8,758,355 B2 | 6/2014 | Fisher |
| 8,771,272 B2 | 7/2014 | Lecronier |
| 8,777,947 B2 | 7/2014 | Zahrly et al. |
| 8,777,995 B2 | 7/2014 | McClintock |
| 8,790,343 B2 | 7/2014 | McClellan |
| 8,790,409 B2 | 7/2014 | Van den Heuvel et al. |
| 8,828,058 B2 | 9/2014 | Elsebaie |
| 8,828,087 B2 | 9/2014 | Stone |
| 8,840,651 B2 | 9/2014 | Reiley |
| 8,870,881 B2 | 10/2014 | Rezach |
| 8,870,959 B2 | 10/2014 | Arnin |
| 8,894,663 B2 | 11/2014 | Giger et al. |
| 8,915,915 B2 | 12/2014 | Harrison |
| 8,915,917 B2 | 12/2014 | Doherty |
| 8,920,422 B2 | 12/2014 | Homeier |
| 8,945,188 B2 | 2/2015 | Rezach |
| 8,961,521 B2 | 2/2015 | Keefer |
| 8,961,567 B2 | 2/2015 | Hunziker |
| 8,968,402 B2 | 3/2015 | Myers |
| 8,968,406 B2 | 3/2015 | Arnin |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher |
| 9,078,703 B2 | 7/2015 | Arnin |
| 2001/0034524 A1 | 10/2001 | Bales |
| 2002/0050112 A1 | 5/2002 | Koch et al. |
| 2002/0072758 A1 | 6/2002 | Reo |
| 2002/0111629 A1 | 8/2002 | Phillips |
| 2002/0143344 A1 | 10/2002 | Taylor |
| 2002/0151898 A1 | 10/2002 | Sohngen et al. |
| 2002/0151978 A1 | 10/2002 | Zacouto et al. |
| 2002/0164905 A1 | 11/2002 | Bryant |
| 2002/0183750 A1 | 12/2002 | Buhler |
| 2003/0034178 A1 | 2/2003 | Cargill et al. |
| 2003/0040671 A1 | 2/2003 | Somogyi |
| 2003/0053855 A1 | 3/2003 | Baur |
| 2003/0069581 A1 | 4/2003 | Stinson |
| 2003/0100378 A1 | 5/2003 | Schwaerzler |
| 2003/0144669 A1 | 7/2003 | Robinson |
| 2003/0195515 A1 | 10/2003 | Sohngen |
| 2003/0204274 A1 | 10/2003 | Ullestad et al. |
| 2003/0220643 A1 | 11/2003 | Ferree |
| 2003/0220644 A1 | 11/2003 | Thelen et al. |
| 2004/0011137 A1 | 1/2004 | Hnat |
| 2004/0011365 A1 | 1/2004 | Govari |
| 2004/0019353 A1 | 1/2004 | Freid |
| 2004/0023623 A1 | 2/2004 | Stauch et al. |
| 2004/0030395 A1 | 2/2004 | Blunn et al. |
| 2004/0055610 A1 | 3/2004 | Forsell |
| 2004/0133219 A1 | 7/2004 | Forsell |
| 2004/0138663 A1 | 7/2004 | Kosashvili et al. |
| 2004/0138725 A1 | 7/2004 | Forsell |
| 2004/0193266 A1 | 9/2004 | Meyer |
| 2005/0012617 A1 | 1/2005 | DiSilvestro et al. |
| 2005/0034705 A1 | 2/2005 | McClendon |
| 2005/0049617 A1 | 3/2005 | Chatlynne |
| 2005/0055025 A1 | 3/2005 | Zacouto et al. |
| 2005/0065529 A1 | 3/2005 | Liu et al. |
| 2005/0090823 A1 | 4/2005 | Bartimus |
| 2005/0107787 A1 | 5/2005 | Kutsenko |
| 2005/0109097 A1 | 5/2005 | Bogath et al. |
| 2005/0159637 A9 | 7/2005 | Nelson et al. |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka |
| 2006/0004447 A1 | 1/2006 | Mastrorio |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0052782 A1 | 3/2006 | Morgan et al. |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0085043 A1 | 4/2006 | Stevenson |
| 2006/0136062 A1 | 6/2006 | Dinello |
| 2006/0142767 A1 | 6/2006 | Green |
| 2006/0155279 A1 | 7/2006 | Ogilvie |
| 2006/0195087 A1 | 8/2006 | Sacher |
| 2006/0195088 A1 | 8/2006 | Sacher |
| 2006/0200134 A1 | 9/2006 | Freid |
| 2006/0204156 A1 | 9/2006 | Takehara |
| 2006/0235299 A1 | 10/2006 | Martinelli |
| 2006/0235424 A1 | 10/2006 | Vitale et al. |
| 2006/0241746 A1 | 10/2006 | Shaoulian |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams |
| 2007/0015622 A1 | 1/2007 | Stauch |
| 2007/0016202 A1 | 1/2007 | Kraft et al. |
| 2007/0021644 A1 | 1/2007 | Woolson |

(56) References Cited

U.S. PATENT DOCUMENTS

| | | |
|---|---|---|
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina |
| 2007/0173837 A1 | 7/2007 | Chan et al. |
| 2007/0179493 A1 | 8/2007 | Kim |
| 2007/0185374 A1 | 8/2007 | Kick |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0244488 A1 | 10/2007 | Metzger et al. |
| 2007/0255088 A1 | 11/2007 | Jacobson |
| 2007/0264605 A1 | 11/2007 | Belfor et al. |
| 2007/0270803 A1 | 11/2007 | Giger et al. |
| 2007/0276368 A1 | 11/2007 | Trieu |
| 2007/0276369 A1 | 11/2007 | Allard |
| 2007/0276373 A1 | 11/2007 | Malandain |
| 2007/0276378 A1 | 11/2007 | Harrison et al. |
| 2007/0276493 A1 | 11/2007 | Malandain |
| 2007/0288024 A1 | 12/2007 | Gollogly |
| 2007/0288183 A1 | 12/2007 | Bulkes et al. |
| 2008/0009792 A1 | 1/2008 | Henniges |
| 2008/0015577 A1 | 1/2008 | Loeb |
| 2008/0021454 A1 | 1/2008 | Chao |
| 2008/0021455 A1 | 1/2008 | Chao |
| 2008/0021456 A1 | 1/2008 | Gupta |
| 2008/0027436 A1 | 1/2008 | Cournoyer |
| 2008/0033431 A1 | 2/2008 | Jung |
| 2008/0033436 A1 | 2/2008 | Song et al. |
| 2008/0048855 A1 | 2/2008 | Berger |
| 2008/0051784 A1 | 2/2008 | Gollogly |
| 2008/0065181 A1 | 3/2008 | Stevenson |
| 2008/0082118 A1 | 4/2008 | Edidin |
| 2008/0086128 A1 | 4/2008 | Lewis |
| 2008/0097487 A1 | 4/2008 | Pool |
| 2008/0097496 A1 | 4/2008 | Chang |
| 2008/0100878 A1 | 5/2008 | Hunter et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower |
| 2009/0030462 A1 | 1/2009 | Buttermann |
| 2009/0062798 A1 | 3/2009 | Conway |
| 2009/0076597 A1 | 3/2009 | Dahlgren et al. |
| 2009/0082815 A1 | 3/2009 | Zylber |
| 2009/0088803 A1 | 4/2009 | Justis |
| 2009/0093820 A1 | 4/2009 | Trieu |
| 2009/0093890 A1 | 4/2009 | Gelbart |
| 2009/0112207 A1 | 4/2009 | Walker et al. |
| 2009/0112262 A1 | 4/2009 | Pool |
| 2009/0112263 A1 | 4/2009 | Pool et al. |
| 2009/0125062 A1 | 5/2009 | Arnin |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips |
| 2009/0216113 A1 | 8/2009 | Meier |
| 2009/0254088 A1 | 10/2009 | Soubeiran |
| 2009/0275984 A1 | 11/2009 | Kim et al. |
| 2010/0004654 A1 | 1/2010 | Schmitz |
| 2010/0049204 A1 | 2/2010 | Soubeiran |
| 2010/0057127 A1 | 3/2010 | McGuire |
| 2010/0094302 A1 | 4/2010 | Pool et al. |
| 2010/0094306 A1 | 4/2010 | Chang et al. |
| 2010/0100185 A1 | 4/2010 | Trieu et al. |
| 2010/0100329 A1 | 4/2010 | Ekseth et al. |
| 2010/0106192 A1 | 4/2010 | Barry |
| 2010/0114322 A1 | 5/2010 | Clifford |
| 2010/0121323 A1 | 5/2010 | Pool et al. |
| 2010/0130941 A1 | 5/2010 | Conlon |
| 2010/0137872 A1 | 6/2010 | Kam |
| 2010/0145449 A1 | 6/2010 | Makower |
| 2010/0145462 A1 | 6/2010 | Ainsworth |
| 2010/0168751 A1 | 7/2010 | Anderson |
| 2010/0228167 A1 | 9/2010 | Ilovich et al. |
| 2010/0228357 A1 | 9/2010 | Stauch |
| 2010/0249782 A1 | 9/2010 | Durham |
| 2010/0249837 A1 | 9/2010 | Seme |
| 2010/0249847 A1 | 9/2010 | Jung et al. |
| 2010/0256626 A1 | 10/2010 | Muller |
| 2010/0262239 A1 | 10/2010 | Boyden |
| 2010/0318129 A1 | 12/2010 | Seme et al. |
| 2010/0331883 A1 | 12/2010 | Schmitz |
| 2011/0004076 A1 | 1/2011 | Janna |
| 2011/0057756 A1 | 3/2011 | Marinescu et al. |
| 2011/0066188 A1 | 3/2011 | Seme |
| 2011/0098748 A1 | 4/2011 | Jangra |
| 2011/0152725 A1 | 6/2011 | Demir |
| 2011/0196435 A1 | 8/2011 | Forsell |
| 2011/0202138 A1 | 8/2011 | Shenoy |
| 2011/0230883 A1 | 9/2011 | Zahrly et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron |
| 2012/0157996 A1 | 6/2012 | Walker |
| 2012/0158061 A1 | 6/2012 | Koch |
| 2012/0172883 A1 | 7/2012 | Sayago |
| 2012/0179215 A1 | 7/2012 | Soubeiran |
| 2012/0203282 A1 | 8/2012 | Sachs et al. |
| 2012/0209265 A1 | 8/2012 | Pool |
| 2012/0221106 A1 | 8/2012 | Makower |
| 2012/0271353 A1 | 10/2012 | Barry |
| 2012/0283781 A1 | 11/2012 | Arnin |
| 2012/0296234 A1 | 11/2012 | Wilhelm et al. |
| 2012/0329882 A1 | 12/2012 | Messersmith et al. |
| 2013/0013066 A1 | 1/2013 | Landry |
| 2013/0072932 A1 | 3/2013 | Stauch |
| 2013/0123847 A1 | 5/2013 | Anderson |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening |
| 2013/0178903 A1 | 7/2013 | Abdou |
| 2013/0211521 A1 | 8/2013 | Shenoy |
| 2013/0245692 A1 | 9/2013 | Hayes |
| 2013/0253344 A1 | 9/2013 | Griswold et al. |
| 2013/0253587 A1 | 9/2013 | Carls |
| 2013/0261672 A1 | 10/2013 | Horvath |
| 2013/0296863 A1 | 11/2013 | Globerman |
| 2013/0296864 A1 | 11/2013 | Burley |
| 2013/0296940 A1 | 11/2013 | Northcutt et al. |
| 2013/0325006 A1 | 12/2013 | Michelinie |
| 2013/0325071 A1 | 12/2013 | Niemiec |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter |
| 2014/0058450 A1 | 2/2014 | Arlet |
| 2014/0066987 A1 | 3/2014 | Hestad |
| 2014/0088715 A1 | 3/2014 | Ciupik |
| 2014/0128920 A1 | 5/2014 | Kantelhardt |
| 2014/0142631 A1 | 5/2014 | Hunziker |
| 2014/0163664 A1 | 6/2014 | Goldsmith |
| 2014/0236234 A1 | 8/2014 | Kroll |
| 2014/0236311 A1 | 8/2014 | Vicatos et al. |
| 2014/0257412 A1 | 9/2014 | Patty |
| 2014/0277446 A1 | 9/2014 | Clifford |
| 2014/0296918 A1 | 10/2014 | Fening et al. |
| 2014/0303538 A1 | 10/2014 | Baym |
| 2014/0303539 A1 | 10/2014 | Baym et al. |

(56) References Cited

U.S. PATENT DOCUMENTS

| | | |
|---|---|---|
| 2014/0324047 A1 | 10/2014 | Zahrly et al. |
| 2014/0358150 A1 | 12/2014 | Kaufman et al. |
| 2015/0105782 A1 | 4/2015 | D'Lima |
| 2015/0105824 A1 | 4/2015 | Moskowitz et al. |

FOREIGN PATENT DOCUMENTS

| | | |
|---|---|---|
| CN | 101040807 A | 9/2007 |
| CN | 101437569 A | 8/2013 |
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 68515687 | 12/2007 |
| DE | 102005045070 | 12/2007 |
| EP | 0663184 A | 7/1995 |
| EP | 1905388 | 4/2008 |
| FR | 2901991 | 12/2007 |
| FR | 2900563 B1 | 8/2008 |
| FR | 2892617 B1 | 9/2008 |
| FR | 2916622 B1 | 9/2009 |
| FR | 2961386 A1 | 12/2011 |
| JP | 0956736 A | 3/1997 |
| JP | 11506345 A | 6/1999 |
| JP | 2001507608 | 6/2001 |
| JP | 2002500063 A | 1/2002 |
| JP | 2003172372 | 6/2003 |
| JP | 2003530195 | 10/2003 |
| RU | 1782564 | 12/1992 |
| RU | 2272594 | 3/2006 |
| SU | 1528471 | 12/1989 |
| SU | 1782564 | 12/1992 |
| WO | 1996002201 A1 | 2/1996 |
| WO | WO199830163 | 7/1998 |
| WO | 1998044858 A1 | 10/1998 |
| WO | WO9951160 | 10/1999 |
| WO | 1999058065 A1 | 11/1999 |
| WO | 2001024697 A1 | 4/2001 |
| WO | 2001045487 A2 | 6/2001 |
| WO | 2001067973 A2 | 9/2001 |
| WO | WO2001078614 | 10/2001 |
| WO | 2001045485 A3 | 1/2002 |
| WO | 2005092219 A1 | 10/2005 |
| WO | WO2006090380 | 8/2006 |
| WO | WO2007015239 | 2/2007 |
| WO | WO2007025191 | 3/2007 |
| WO | WO2007118179 | 10/2007 |
| WO | WO2007144489 | 12/2007 |
| WO | WO2008003952 | 1/2008 |
| WO | WO2008040880 | 4/2008 |
| WO | 2007013059 A3 | 4/2009 |
| WO | WO2009058546 | 5/2009 |
| WO | 2011116158 A3 | 1/2012 |
| WO | 2013119528 A1 | 8/2013 |
| WO | 2014040013 A1 | 3/2014 |

OTHER PUBLICATIONS

Written Opinion for PCT/US2010/047842, ISA, dated Nov. 4, 2010, p. 6.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

International Commission on Non-Ionizing Radiation Protection {ICNIRP), "Guidelines Limiting Exposure to Time-Varying Electric, Magnetic, and Electromagnetic Fields (Up to 300 GHz)", Health Physics, 1998, vol. 74, No. 4, pp. 494-522.

International Commission on Non-Ionizing Radiation Protection (ICNIRP), "Guidelines on Limits of Exposure to Static Magnetic Fields". Health Physics 2009, vol. 96, No. 4, pp. 504-514.

PCT International Search Report for PCT/US2010/047842, Applicant: Ellipse Technologies, Inc., Form PCT/ISA/210 and 220, dated Nov. 4, 2010 (4 pages).

PCT Written Opinion of the International Search Authority for PCT/US2010/047842, Applicant: Ellipse Technologies, Inc., Form PCT/ISA/237, dated Nov. 4, 2010 (6 pages).

Cole, J., Paley, D., Dahl, M., "Operative Technique. ISKD. Intramedullary Skeletal Kinetic Distractor. Tibial Surgical Technique" IS-0508(A)-OPT-US © Orthofix Inc. Nov. 2005 (28 pages).

Gebhardt, M., Neel, M., Souberian, A., Dubousset, J., "Early clinical experience with a custom made growing endoprosthesis in children with malignant bone tumors of the lower extremity actioned by an external permanent magnet: The Phenix M system", International Society of Limb Salvage 14International Symposium on Limb Salvage, Sep. 13, 2007, Hamburo, Germany. (2 pages).

Notice of Allowance in Russian Patent Application No. 2012112925 (ELPSE.009RU) dated Sep. 15, 2015 in 4 pages.

Guichet, J., Deromedis, B., Donnan, L, Peretti, G., Lascombes, P., Bado, F., "Gradual Femoral Lengthening with the Albizzia Intramedullary Nail", Journal of Bone and Joint Surgery American Edition, 2003, vol. 85, pp. 838-848 (12 pages).

Gray's Anatomy, http://education.yahoo.com/reference/gray/subjects/subject/128, published Jun. 12, 2012.

Grimer, R., Chotel, F., Abudu, S., Tilman, R., Carter, S., "Non-invasive extendable endoprosthesis for children—expensive but worth it!", International Society of Limb Salvage 14th International Symposium on Limb Salvaae, Sep. 13, 2007, Hambura, Germany. (1 page).

Gupta, A., Meswania, J., Pollock, R., Cannon, S., Briggs, T., Taylor, S., Blunn, G., "Non-Invasive distal Femoral Expandable Endoprosthesis for Limb-Salvage Surgery in Pardiatric Tumours", The Journal of Bone and Joint Surgery British Edition, 2006, vol. 88-B, No. 5, pp. 649-654, Churchill Livingstone, London, England. (6 pages).

Hankemeier, S., Gosling, T., Pape, H., Wiebking, U., Krettek, C., "Limb Lengthening with the Intramedullary Sketal Kinetic Distractor (ISKD)", Operative Orthopadie und Traumatologie, 2005, vol. 17, No. 1, pp. 79-101, Urban & Vogel, Munich, Germany. (23 pages).

Prontes, Isabel, http://www.ehow.com/about_4795793_longest-bone-body.html, published Jun. 12, 2012.

Sharke, P., "the Machinery of Life", mechanical Engineering Magazine, Feb. 2004, Printed from Internet Site Oct. 24, 2007 http://www.memagazine.org/contents/current/features/moflife/moflife.html (10 pages}.

Soubeiran, A., Gebhart, M., Miladi, L., Griffet, J., Neel, M., Dubousset, J., "The Phenix M System. A fully implanted Lenthenging Device Externally Controllable Through the Skin with a Palm Size with a Palm Size Permanent Magnet; Applications to Pediatric Orthopaedics", 5th European Research Conference in Pediatric Orthopaedics, Oct. 6, 2006, Toulouse, France. (7 pages).

Soubeiran, A., Gebhart, M., Miladi, L., Griffet, J., Neel, M., Dubousset, J., "The Phenix M System. A fully implanted non-implanted non-invasive lengthening device externally controllable through the skin with a palm size permanent magnet. Applications in Limb salvage" International Society of Limb Salvage 14th International Symposium on Limb Salvage, Sep. 13, 2007, Hamburg, Germany. (2 pages).

Verkerke, G. Koops, H., Veth, R. Oldhoff, J., Nielson, H., vanden Kroonenberg, H., Grootenboer, H., van Krieken, F., "Design of a Lengthening Element for a Modular Femur Endoprosthetic System", Proceedings of the Institution of Mechanical Engineers Part H: Journal of Engineering in Medicine, 1989, vol. 203, No. 2, pp. 97-102, Mechanical Engineering Publications, London, England. (6 pages).

Verkerke, G., Koops, H., Veth, R., van den Kroonenberg, H., Grootenboer, H., Nielsen, H., Oldhoff, J., Postma, A., "An Extendable Modular Endoprosthetic System for Bone Tumor Management in the Leg", Journal of Biomedical Engineering, 1990, vol. 12, No. 2, pp. 91-96, Butterfield Scientific Limited, Gulford, England (6 pages}.

(56) References Cited

OTHER PUBLICATIONS

Abe et al., "Experimental external fixation combined with percutaneous discectomy in the management of scoliosis.", Spine, 1999, pp. 646-653, 24, No. 7.
Ahlbom et al., "Guidelines for limiting exposure to time-varying electric, magnetic, and electromagnetic fields (up to 300 GHz), International Commission on Non-Ionizing Radiation Protection.", Health Physics, 1998, pp. 494-522, 74, No. 4.
Amer et al., "Evaluation of treatment of late-onset tibia vara using gradual angulation translation high tibial osteotomy", ACTA Orthopaedica Belgica, 2010, pp. 360-366, 76, No. 3.
Angrisani et al., "Lap-Band® Rapid Port™ System: Preliminary results in 21 patients", Obesity Surgery, 2005, p. 936, 15, No. 7.
Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandabie prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012. pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. SI05-SII5, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta, et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am. 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Aibizzia nail.", Practice of Intramedullary Locked Nails, 2006, pp. 211-215.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
International Search Report for PCT/US2010/047842, ISA, dated Nov. 4, 2010, pp. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.

(56) References Cited

OTHER PUBLICATIONS

Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?.", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Rospatent, Notice of Allowance in RU2012112925 dated Sep. 15, 2015.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, p. 511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013 Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 23 pgs.
Takaso et al., "New remote-controlled growing-rod spinal instrumentation possibly applicable for scoliosis in young children.", Journal of Orthopaedic Science, 1998, pp. 336-340, 3, No. 6.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX@)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.

(56) References Cited

OTHER PUBLICATIONS

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
Brown et al., "Single port surgery and the Dundee Endocone.", SAGES Annual Scientific Sessions: Emerging Technology Poster Abstracts, 2007, ETP007, pp. 323-324.
Ember et al., "Distraction forces required during growth rod lengthening.", J of Bone Joint Surg BR, 2006, p. 229, 88-B, No. Suppl. II.
Horbach et al., "First experiences with the routine use of the Rapid Port™ system with the Lap-Band®.", Obesity Surgery, 2006, p. 418, 16, No. 4.
Micromotion, "Micro Drive Engineering General catalogue.", 2009, pp. 14-24.
Teli et al., "Measurement of forces generated during distraction of growing rods.", Journal of Children's Orthopaedics, 2007, pp. 257-258, 1, No. 4.

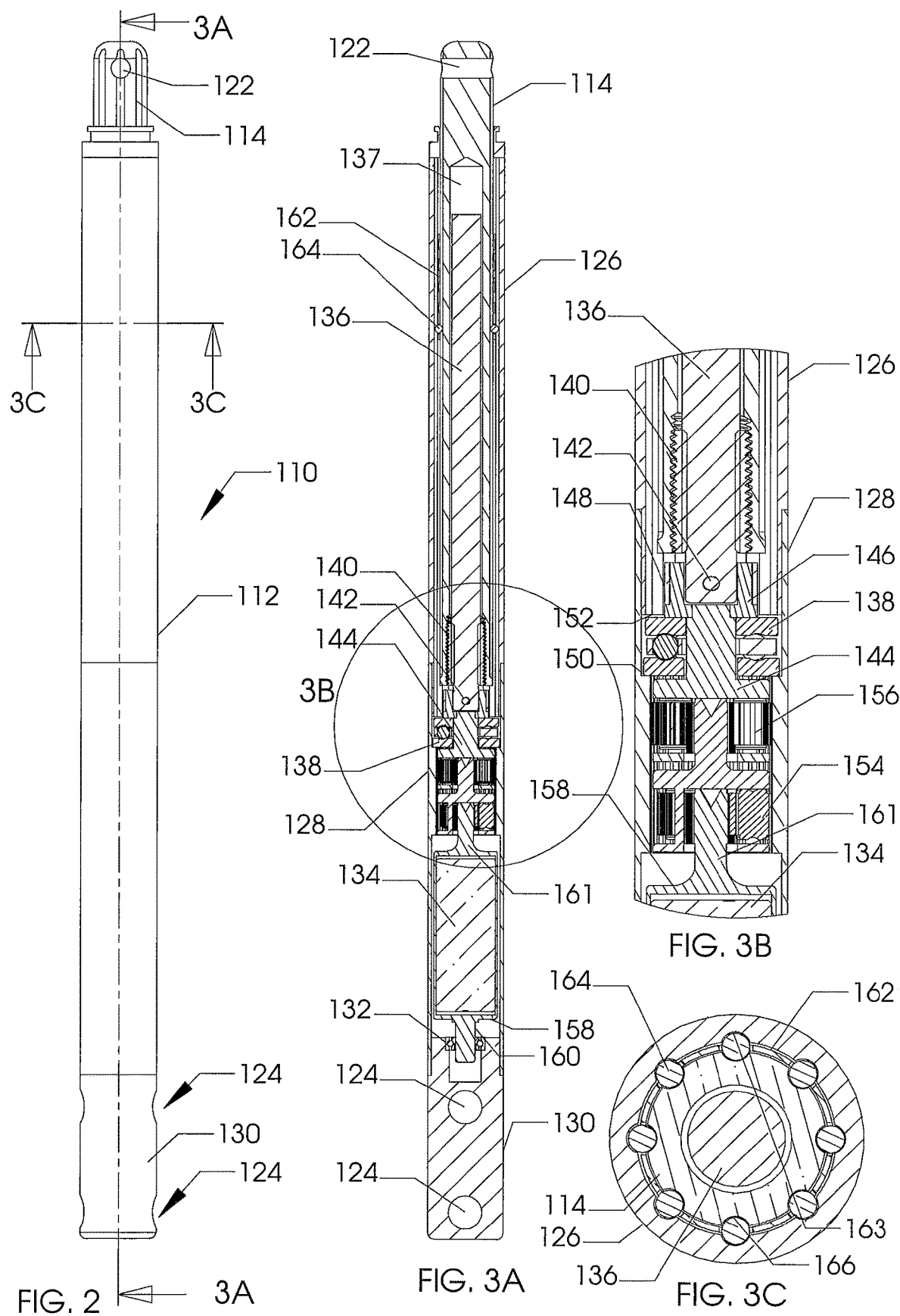

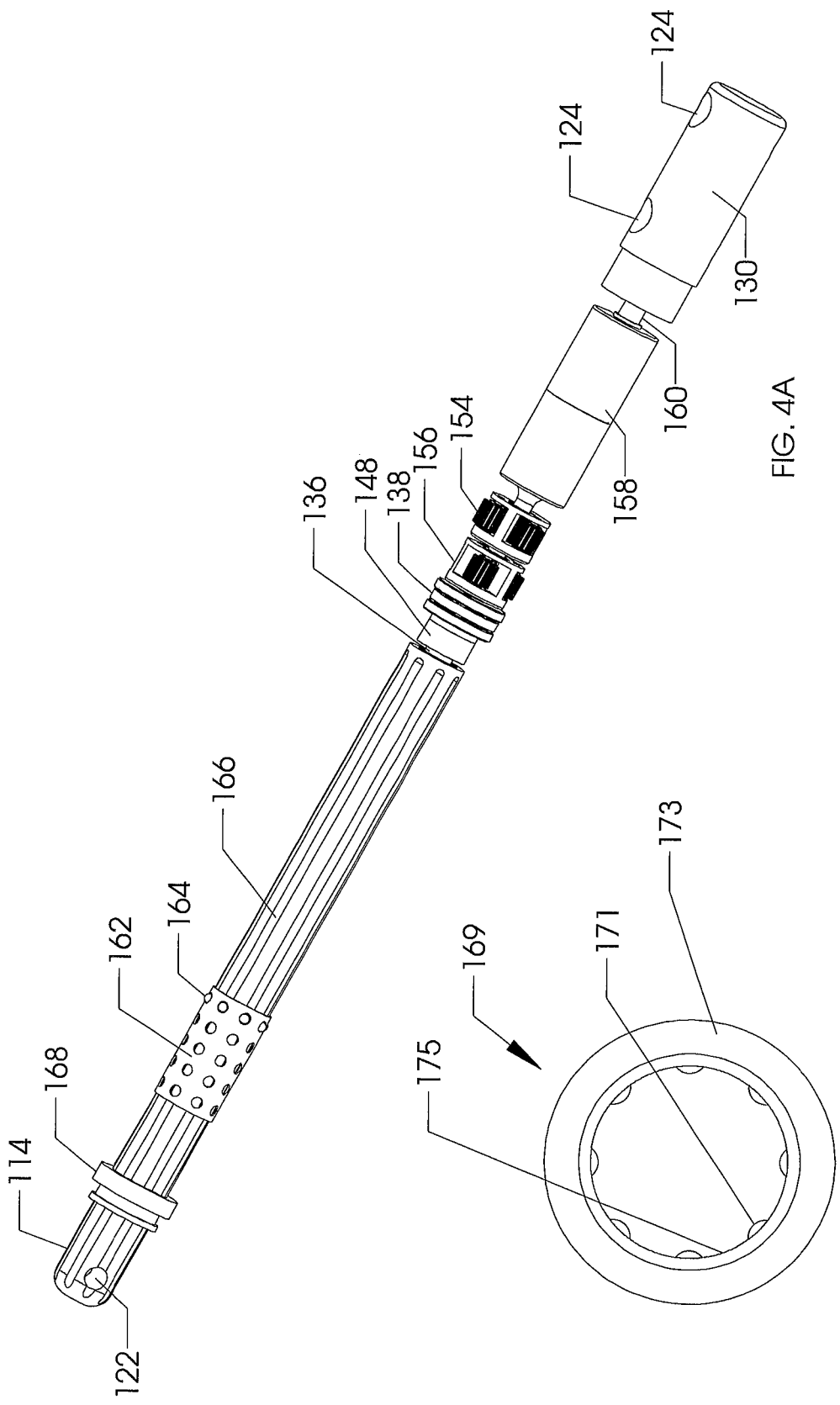

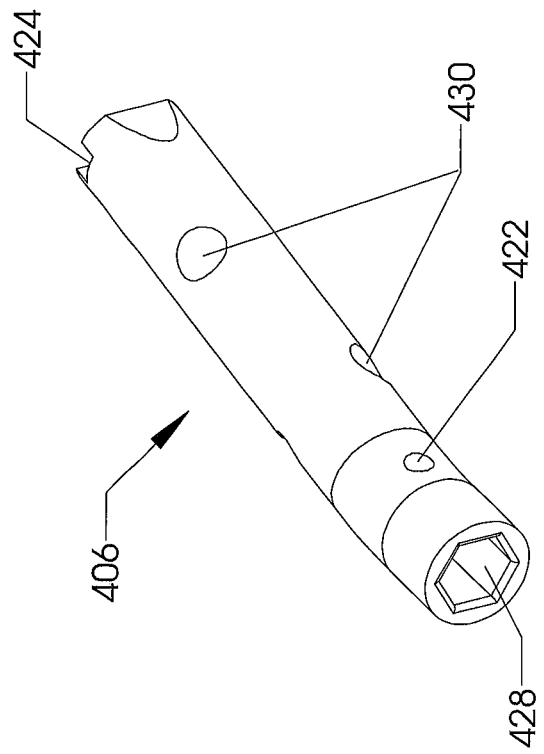
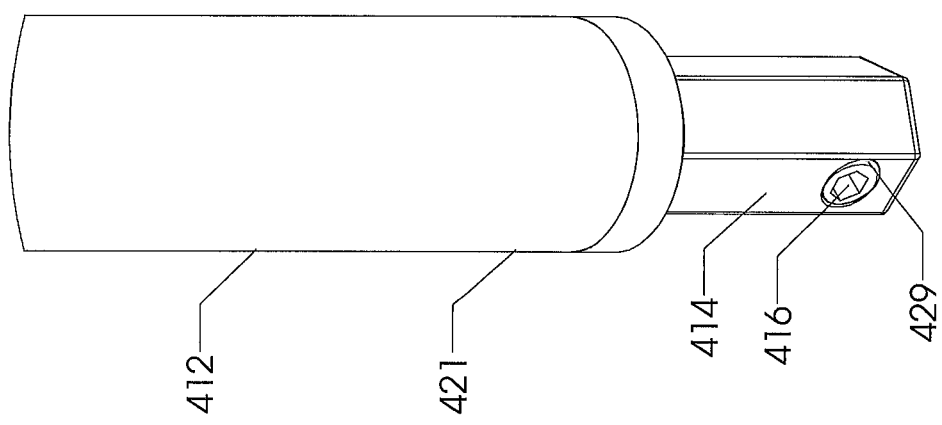

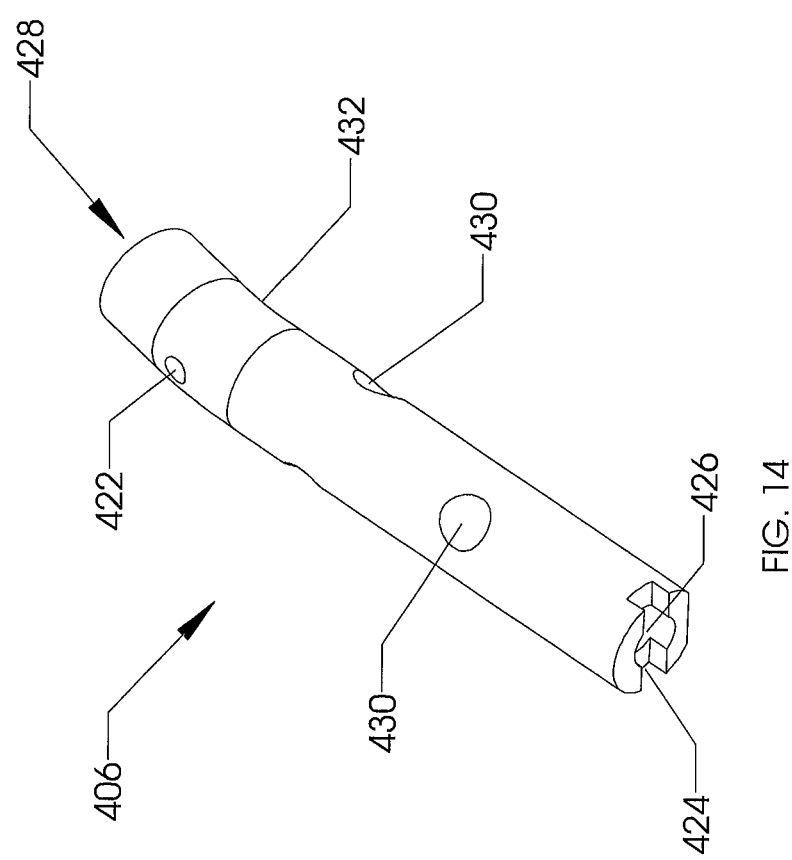

BONE GROWTH DEVICE AND METHOD

RELATED APPLICATIONS

Any and all applications for which a foreign or domestic priority claim is identified in the Application Data Sheet as filed with the present application are hereby incorporated by reference under 37 CFR 1.57.

FIELD OF THE INVENTION

The field of the invention generally relates to medical devices for treating conditions involving the skeletal system and in particular bone growth applications.

BACKGROUND OF THE INVENTION

Distraction osteogenesis, also known as distraction callotasis and osteodistraction has been used successfully to lengthen long bones of the body. Typically, the bone, if not already fractured, is purposely fractured by means of a corticotomy, and the two segments of bone are gradually distracted apart, which allows new bone to form in the gap. If the distraction rate is too high, there is a risk of nonunion, if the rate is too low, there is a risk that the two segments will completely fuse to each other before the distraction period is complete. When the desired length of the bone is achieved using this process, the bone is allowed to consolidate. Distraction osteogenesis applications are mainly focused on the growth of the femur or tibia, but may also include the humerus, the jaw bone (micrognathia), or other bones. The reasons for lengthening or growing bones are multifold, the applications including, but not limited to: post osteosarcoma bone cancer, cosmetic lengthening (both legs-femur and/or tibia) in short stature or dwarfism/achondroplasia; lengthening of one limb to match the other (congenital, post-trauma, post-skeletal disorder, prosthetic knee joint), nonunions.

Distraction osteogenesis using external fixators has been done for many years, but the external fixator can be unwieldy for the patient. It can also be painful, and the patient is subject to the risk of pin track infections, joint stiffness, loss of appetite, depression, cartilage damage and other side effects. Having the external fixator in place also delays the beginning of rehabilitation.

In response to the shortcomings of external fixator distraction, intramedullary distraction nails have been surgically implanted which are contained entirely within the bone. Some are automatically lengthened via repeated rotation of the patient's limb. This can sometimes be painful to the patient, and can often proceed in an uncontrolled fashion. This therefore makes it difficult to follow the strict daily or weekly lengthening regime that avoids nonunion (if too fast) or early consolidation (if too slow). Lower limb distraction rates are on the order of one millimeter per day. Other intramedullary nails have been developed which have an implanted motor and are remotely controlled. The motorized intramedullary nails have an antenna which needs to be implanted subcutaneously, thus complicating the surgical procedure, and making it more invasive. These devices are therefore designed to be lengthened in a controlled manner, but due to their complexity, may not be manufacturable as an affordable product. Others have proposed intramedullary distractors containing and implanted magnet, which allows the distraction to be driven electromagnetically by an external stator (i.e., a large electromagnet). Because of the complexity and size of the external stator, this technology has not been reduced to a simple and cost-effective device that can be taken home, to allow patients to do daily lenthenings.

SUMMARY OF THE INVENTION

In a first embodiment, a lengthening device is configured for placement inside or across bone having first and second separate sections. The device includes a housing configured for attachment to one of the first and second separate bone sections and a distraction shaft having an internal cavity along a length thereof and configured for attachment to the other of the first and second separate bone sections. The device includes a permanent magnet configured for rotation relative to the housing and having at least two poles, the permanent magnet operatively coupled to a lead screw, the lead screw interfacing with a threaded portion of the internal cavity of the distraction shaft. A thrust bearing is disposed in the housing and interposed between the lead screw and the permanent magnet, the thrust bearing sandwiched between first and second abutments in the housing.

In a second embodiment, a lengthening device is configured for placement inside an intramedullary canal of a bone having first and second separate sections. The device includes a housing configured for attachment to one of the first and second separate bone sections and a distraction shaft having an internal cavity along a length thereof and configured for attachment to the other of the first and second separate bone sections. A permanent magnet is disposed in the housing and configured for rotation and having at least two poles. A planetary gear set having a plurality of gears is provided, wherein one of the gears is operatively coupled to the permanent magnet and configured for transmitting torque, and wherein another gear of the plurality of gears terminates in an output shaft operatively coupled to a lead screw, the lead screw interfacing with a threaded portion of the internal cavity of the distraction shaft.

In a third embodiment, a lengthening system is configured for placement inside an intramedullary canal of a bone. The system includes an actuator with a housing containing a rotatable permanent magnet and moveable distraction shaft telescopically mounted relative the housing, the moveable distraction shaft operatively coupled to the rotatable permanent magnet via a lead screw, wherein a distal end of the distraction shaft is configured for attachment to a first region of the bone and wherein a proximal end of the actuator has a geometrically shaped hub of a male type. The system further includes an extension rod having at one end thereof a geometrically shaped hub of a female type configured to secure to the geometrically shaped hub of the male type disposed on the actuator, wherein an opposing end of the extension rod is configured for attachment to a second region of the bone.

In yet another embodiment, a lengthening system is configured for placement inside an intramedullary canal of a bone. The system includes an actuator with a housing containing a rotatable permanent magnet and a moveable distraction shaft telescopically mounted relative the housing, the moveable distraction shaft operatively coupled to the rotatable permanent magnet via a lead screw, wherein a distal end of the distraction shaft is configured for attachment to a first region of the bone and wherein a proximal end of the actuator comprises a geometrically shaped hub of a female type. The system further includes an extension rod having at one end thereof a geometrically shaped hub of a male type configured to secure to the geometrically shaped hub of the female type disposed on the actuator, wherein an opposing end of the extension rod is configured for attachment to a second region of the bone.

In still another aspect of the invention, an external adjustment device for adjusting an adjustable implant includes a power supply, a control module, and a handheld device comprising at least one permanent magnet. The handheld device is configured to be placed on a first side of a patient's limb and the at least one permanent magnet is configured to turn a cylindrical magnet located inside an adjustable implant. The control module is configured to restrict the number of turns of the cylindrical magnet located inside the adjustable implant.

BRIEF DESCRIPTION OF THE DRAWINGS

FIG. 2 illustrates a side view of the intramedullary lengthening device of FIG. 1.

FIG. 3A illustrates a cross-sectional view of the intramedullary lengthening device of FIGS. 1 and 2 taken along the line 3A-3A of FIG. 2.

FIG. 3B illustrates a detailed view of the intramedullary lengthening device of FIG. 3A from the area of circle 3B.

FIG. 3C illustrates a cross-sectional view of the intramedullary lengthening device of FIGS. 1 and 2 taken along the line 3C in FIG. 2.

FIG. 4A illustrates a view of several of the internal components of the intramedullary lengthening device of the prior FIGS.

FIG. 4B illustrates a lip seal configured for use in the intramedullary lengthening device of the prior FIGS.

FIG. 12 illustrates one end of the actuator of the intramedullary lengthening device of FIG. 11.

FIG. 13 illustrates an extension rod of the modular intramedullary lengthening device.

FIG. 14 illustrates a second view of the extension rod of FIG. 13.

DETAILED DESCRIPTION OF THE ILLUSTRATED EMBODIMENTS

Figure 1:
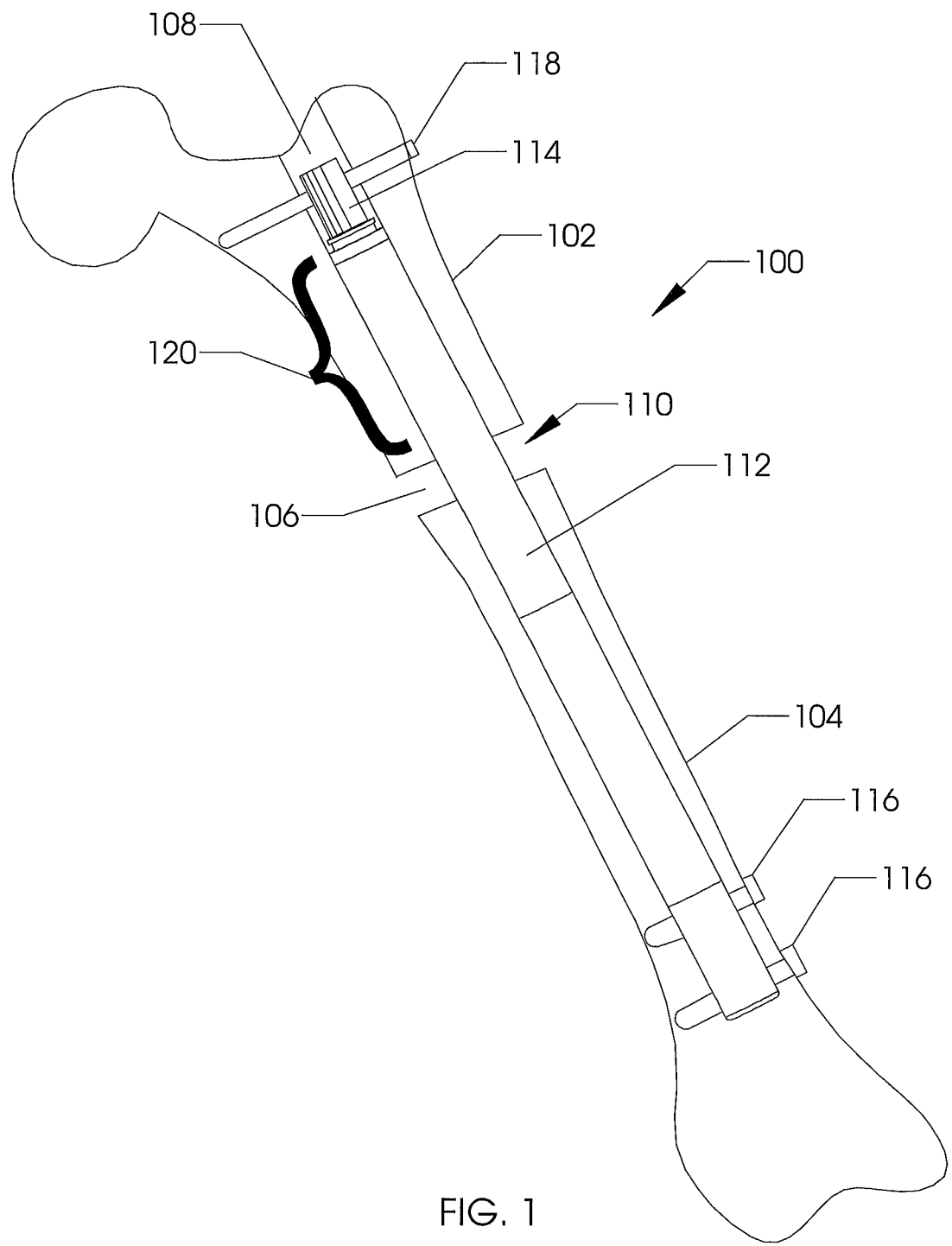
FIG. 1 illustrates side view of an intramedullary lengthening device in place within a bone according to one embodiment.

FIG. 1 illustrates the side view of an intramedullary lengthening device 110 which has been placed through a hole or bore 108 contained within a bone 100. The hole or bore 108 may be made by drilling, reaming and the like and may extend through both cortical bone (at the end) and through cancellous (spongy) bone. The intramedullary lengthening device 110 illustrated in FIG. 1 includes a housing 112 and a distraction shaft 114. In order to grow or lengthen the bone 100, the bone 100 either has a pre-existing separation 106 or is purposely cut or broken to create this separation 106, dividing the bone into a first section 102 and a second section 104. The cut may be done prior to inserting and securing the intramedullary lengthening device 110, or may be done after the device 110 is inserted, for example by use of a flexible Gigli saw. The distraction shaft 114 of the intramedullary lengthening device 110 is attached to the first section 102 using one or more attachment screws 118. Fasteners other than screws 118 known to those skilled in the art may also be used to secure the distraction shaft 114 to the first section 102 of the bone 100. The housing 112 of the intramedullary lengthening device 110 is secured to the second section 104 of bone 100 using one or more attachment screws 116. Again, fasteners other than screws 116 may be used to secure the housing 112 to the second section 104 of bone 100.

Over the treatment period, the bone 100 is continually distracted, creating a new separation 106, into which osteogenesis can occur. Continually distracted is meant to indicate that distraction occurs on a regular basis which may be on the order of every day or every few days. An exemplary distraction rate is one millimeter per day although other distraction rates may be employed. That is to say, a typical distraction regimen may include a daily increase in the length of the intramedullary lengthening device 110 by about one millimeter. This may be done, for example, by four lengthening periods per day, each having 0.25 mm of lengthening. The intramedullary lengthening device 110, as will be shown in the following FIGS., has a magnetic drive system, which allows the distraction shaft 114 to be telescopically extended from the housing 112, thus forcing the first section 102 and the second section 104 of the bone 100 apart from one another. As the distraction is performed, a portion of the housing 112 is able to slide within the hole or bore 108 of the first section 102 if bone 100 within a displacement section 120. The orientation of the intramedullary lengthening device 110 within the bone may be opposite of that shown in FIG. 1. For example, the distraction shaft 114 may be coupled to the second section 104 of the bone 100 and the housing 112 may be coupled to the first section 102 of the bone 100. For example, the intramedullary lengthening device 110 may be placed retrograde, from a hole or bore starting at the distal end of the bone 100.

Turning to FIGS. 2 through 5, the intramedullary lengthening device 110 has one or more distraction shaft screw holes 122 in the distraction shaft 114 through which the screws 118 (FIG. 1) may be placed. Likewise, the housing 112 is attached to an end cap 130 which has one or more housing screw holes 124 through which the screws 116 (FIG. 1) may be placed. The housing 112 of the intramedullary lengthening device 110 includes a magnet housing 128 and a splined housing 126. These housings 126, 128 may be attached to each other by means of welding, adhesive bonding or other joining techniques. The magnet housing 128 is sealably closed at one end (the end opposite the interface with the splined housing 126) by the attachment of the end cap 130. The end cap 130 may be attached to the magnet housing 128 by means of welding, adhesive bonding or other joining techniques. In use, the distraction shaft 114 is driven from the housing 112 by means of a lead screw 136 which turns inside a nut 140 that is secured to an inner surface adjacent to a cavity 137 of the distraction shaft 114. The lead screw 136 is mechanically coupled, in an indirect manner, to cylindrical permanent magnet 134 contained within the magnet housing 128. As explained in more detail below, rotation of the cylindrical permanent magnet 134, which is magnetically driven by an external adjustment device 180 (FIG. 6), effectuates rotation of the lead screw 136.

Figure 9:
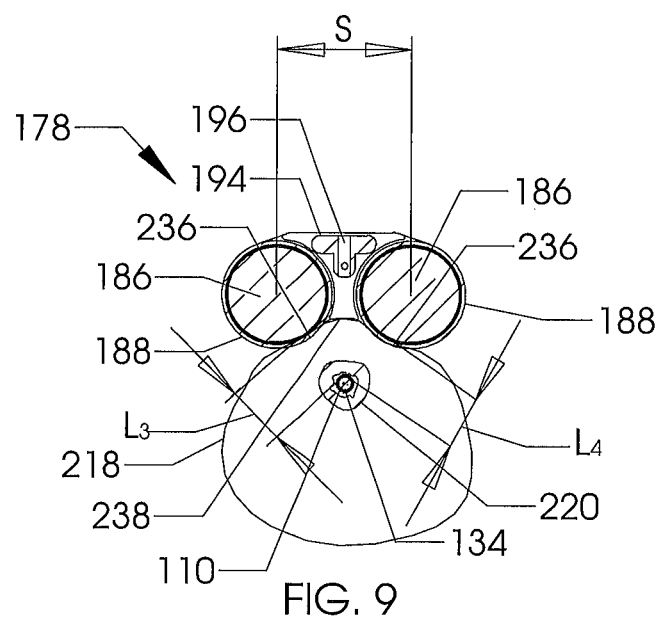
FIG. 9 illustrates a cross-sectional representation of the external adjustment device handpiece of FIGS. 6 and 7 being positioned on a patient's lower thigh.
Figure 19:
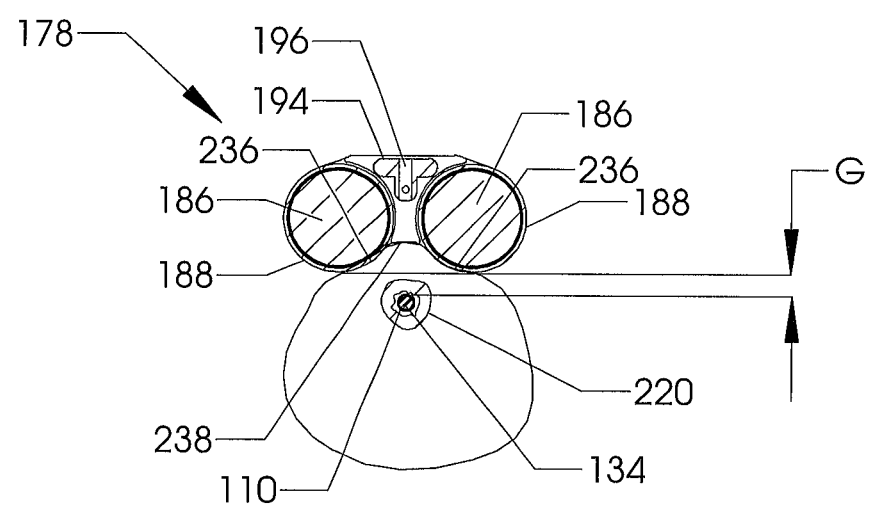
FIG. 19 illustrates a gap (G) between a magnetic handpiece and an intramedullary lengthening device.

Cylindrical magnet 134 is fixedly contained within a magnet casing 158 using, for example, an adhesive such as an epoxy. The magnet casing 158 rotates relative to the magnet housing 128. The cylindrical magnet 134 may be a rare earth magnet such as Nd—Fe—B and may be coated with Parylene or other protective coatings in addition to being protected within the magnet casing 158, for example hermetically potted with epoxy. The magnet casing 158 contains an axle 160 on one end which attaches to the interior of a radial bearing 132. The outer diameter of the radial bearing 132 is secured to the interior of the end cap 130. This arrangement allows the cylindrical magnet 134 to rotate with minimal torsional resistance. At its other, opposing end, the magnet housing 158 includes an axle 161, which is attached to a first planetary gear set 154. The axle 161 includes the sun gear of the first planetary gear set 154, the sun gear turning the planetary gears of the first planetary gear set 154. The first planetary gear set 154 serves to reduce the rotational speed and increase the resultant torque delivery from the cylindrical magnet 134 to the lead screw 136. A second planetary gear set 156 is also shown between the first planetary gear set 154 and the lead screw 136, for further speed reduction and torque augmentation. The number of planetary gear sets and/or the number of teeth in the gears may be adjusted, in order to achieve the desired speed and torque delivery. For example, a lead screw with eighty (80) threads per inch attached to two planetary gear sets of 4:1 gear ratio each inside a 9 mm device with magnet location in the distal femur can achieve at least 100 lb. of distraction force at a greater than average distance or gap from the external device (FIG. 9 or FIG. 19). The planetary gear sets 154, 156 output to a planetary gear output shaft 144. The planetary gear output shaft 144 extends through a thrust bearing 138 and is secured (by welding and the like) to a lead screw coupling cap 146. The lead screw 136 is secured to the lead screw coupling cap 146 by a locking pin 142, which extends through a hole in the lead screw 136 and holes in the lead screw coupling cap 146. A locking pin retainer 148 is a cylinder that surrounds the locking pin 142, holding this assembly together. Attaching the lead screw 136 to the rest of the magnet/gear assembly in this manner, assures that the design is not over-constrained, and thus that the lead screw 136 does not gall with the nut 140. In addition, a biocompatible grease, for example KRYTOX, may be used on the moving parts (lead screw, nut, bearings, housing, and distraction shaft) in order to minimize frictional losses. The lead screw 136 is able to freely rotate within a cavity 137 of the distraction shaft 114, and only need engage with the short length of the nut 140, this feature also minimizing frictional losses.

The thrust bearing 138 serves to protect the magnet/gear assembly of the drive from any significant compressive or tensile stresses. The thrust bearing 138 consists of two separate races with ball bearings between the two races. When there is a compressive force on the device, for example, when distracting a bone 100, and thus resisting the tensile strength of the soft tissues, the thrust bearing 138 abuts against a magnet housing abutment or lip 150 located in the magnet housing 128. Additionally, though the device is not typically intended for pulling bones together, there may be some applications where this is desired. For example, in certain compressive nail applications it is the goal to hold two fractured sections of a bone together. Because the bone 100 may have fractured in a non-uniform or shattered pattern, it may be difficult to determine the desired length of the nail until after it is implanted and fully attached. In these situations, it can be easy to misjudge the length, and so a gap may exist between the bones. By placing a slightly extended intramedullary device 110 and securing it, the device 110 may be retracted magnetically, after it has been secured within the bone fragments, so that it applies the desired compression between the two fragments. In these compressive nail applications, there would be tensile force on the device 110 and the thrust bearing 138 would abut against a splined housing abutment or lip 152. In both situations, the thrust bearing 138 and a rigid portion of one of the housing sections take the large stresses, not the magnet/gear assembly of the drive system. In particular, the thrust bearing 138 is sandwiched between the abutment or lip 150 and the abutment or lip 152.

Figure 5:
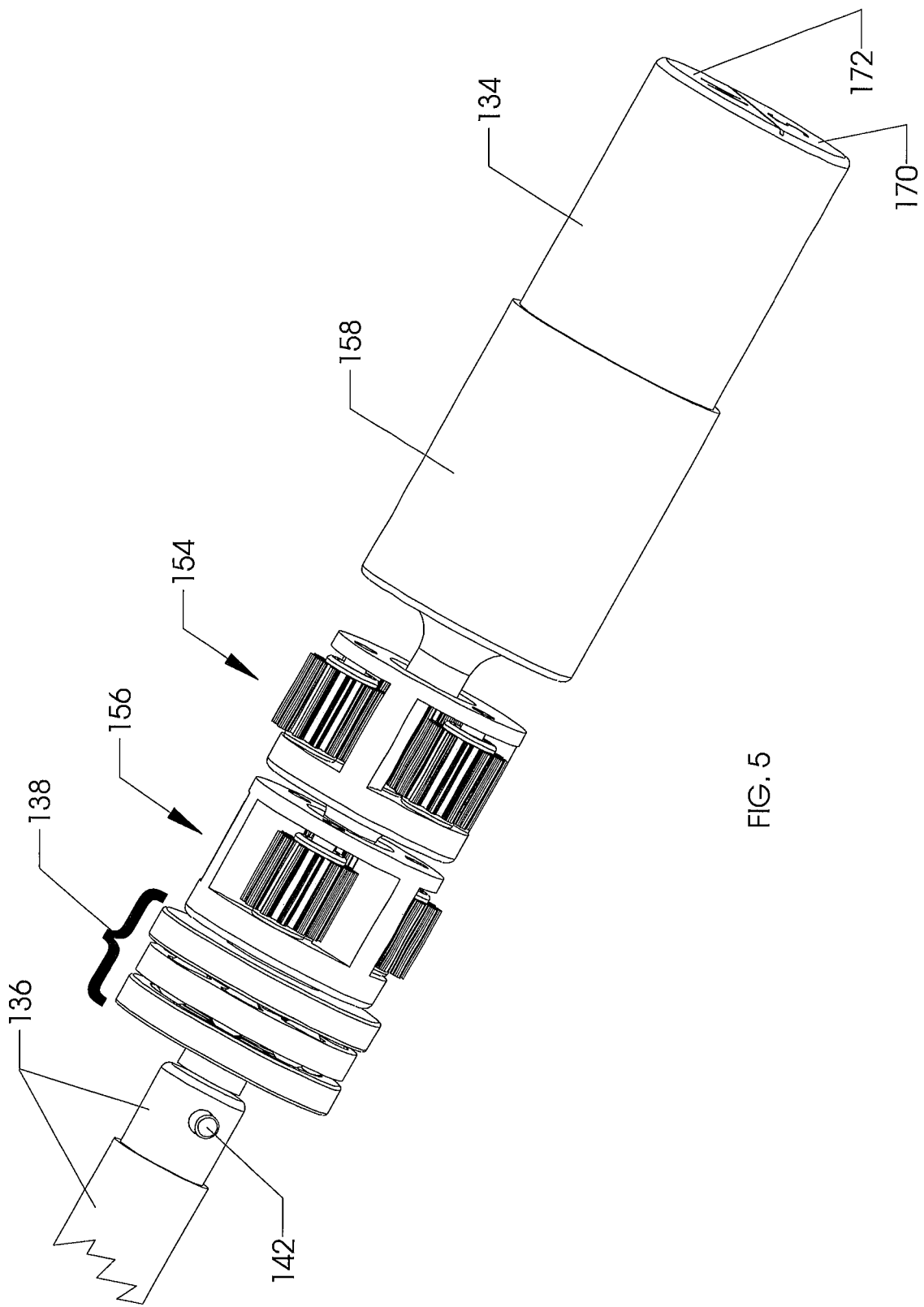
FIG. 5 illustrates a detailed view of several internal components of the drive mechanism of the intramedullary lengthening device of the prior figures.

Turning specifically to FIGS. 4A and 5, the housing components have been removed to reveal various internal features, including a collar that allows sliding of the distraction shaft 114 within the housing 112, and which also keeps the distraction shaft 114 from being able to rotate within the housing 112. This allows full stability of the bone 100. Distraction shaft 114 contains several axial grooves 166. The grooves 166 have semi-circular indentation cross-sections which allow several balls 164 to roll within them. The balls 164 are trapped within a linear ball cage 162. The splined housing 126 which fits over the balls 164 and linear ball cage 162 has axial grooves 163 (FIG. 3C) along its inner diameter surface that are similar to the axial grooves 166 of the distraction shaft 114. In this regard, the balls 164 and the ball cage 162 are interposed between the distraction shaft 114 and the splined housing 126. Therefore, the balls 164 are held in place by the linear ball cage 162, and mechanically lock the respective grooves to each other, thus impeding rotation of the distraction shaft 114 within the housing 112. However, the balls 164 are able to roll within the linear ball cage 162, thus allowing axial displacement of the distraction shaft 114 in relation to the splined housing 126 of the housing 112 with very low friction. A lip seal flange 168 contains a custom cross-section lip seal 169 (shown in FIG. 4B) which allows a sliding seal between the distraction shaft 114 and the splined housing 126, thus protecting the inner contents of the entire assembly from the body environment. The lip seal 169 includes a base portion 173, which seals against the inner diameter of the lip seal flange 168 (and thus the splined housing 126 which is attached to the lip seal flange 168). The lip seal 169 also includes protrusions 171 which slidingly seal against the axial grooves 166 of the distraction shaft 114. Inner surface 175 of the lip seal 169 slidingly seals against the overall outer diameter of the distraction shaft 114. It should also be noted that the lip seal 169 may be made from silicone, EPDM or other rubber materials, and may be coated with silicone oil, to aid in lubricity. Also, the balls, grooves and ball cage may be coated with silicone oil or a liquid perfluorinated polyether such as KRYTOX to aid in lubricity. FIG. 5 shows a portion of the magnet casing 158 removed so that the South pole 170 and North pole 172 of the cylindrical magnet 134 may be illustrated.

Figure 6:
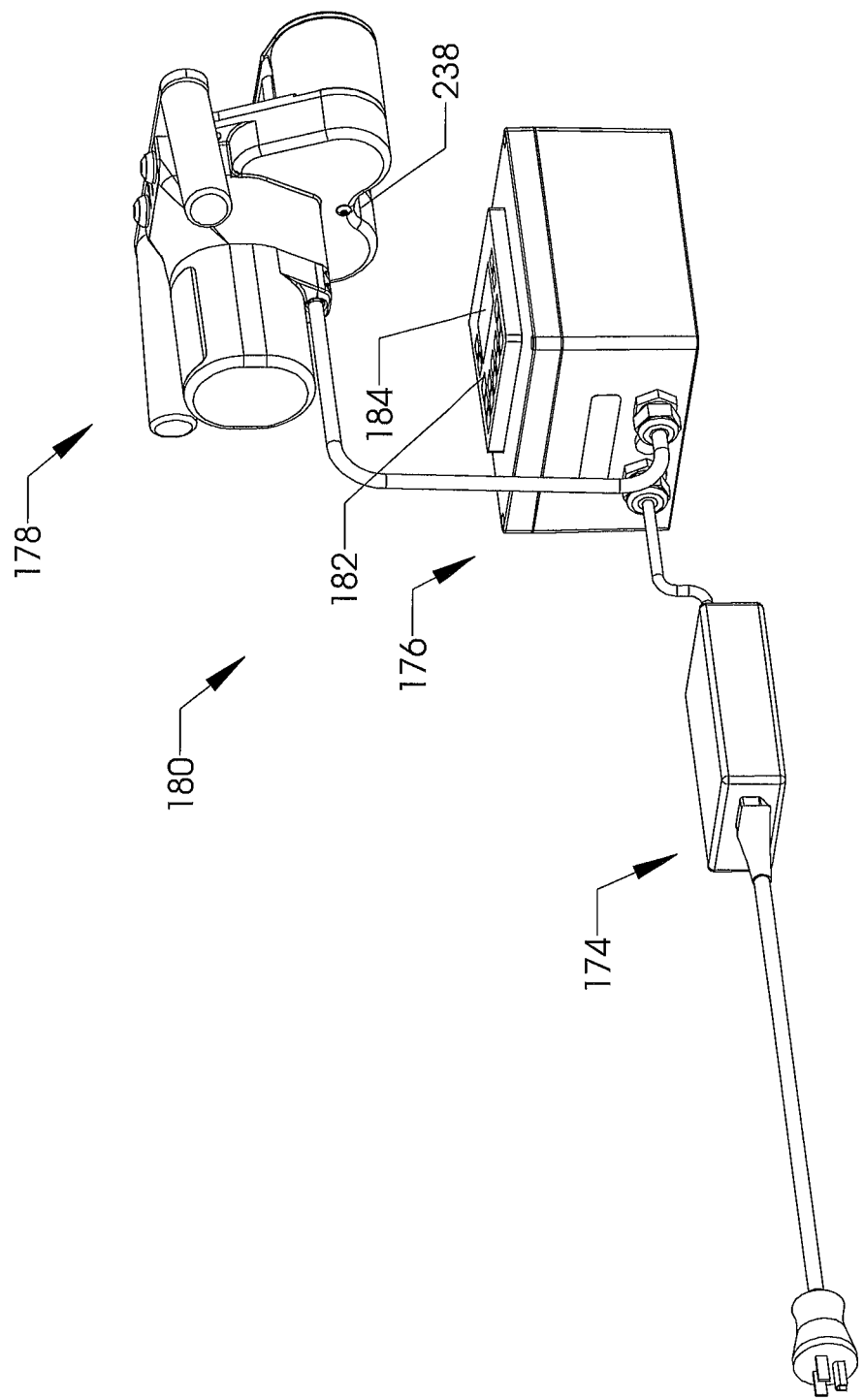
FIG. 6 illustrates a perspective view of an external adjustment device.

FIG. 6 illustrates an external adjustment device 180 which is used to non-invasively distract the intramedullary lengthening device 110 by means of a magnetic coupling which transmits torque. The external adjustment device 180 comprises a magnetic handpiece 178, a control box 176 and a power supply 174. The control box 176 includes a control panel 182 having one or more controls (buttons, switches or tactile, motion, audio or light sensors) and a display 184. The display 184 may be visual, auditory, tactile, the like or some combination of the aforementioned features. The external adjustment device 180 may contain software which allows programming by the physician. For example, the physician may desire that the patient take home the external adjustment device 180 in order that the patient or member of the patient's family or friends make daily distractions of the intramedullary lengthening device 110 implanted in the patient. However, the physician is able to keep the person operating the external adjustment device 180 from over distracting the patient by programming this into the control box 176. For example, the physician may pre-program the control 176 box so that only one (1) mm of distraction is allowed per day. The physician may additionally pre-program the control box 176 so that no more than 0.5 mm may be distracted during any two hour period, or that no more than 0.25 mm may be retracted during a five minute period. Settings such as these may serve to assure that the patient not be capable of causing severe damage to the bone or tissue, nor disrupt the lengthening process.

Preferably, such instructions or limits may be pre-programmed by the physician or even the manufacturer in a secure fashion such that user cannot alter the pre-programmed setting(s). For example, a security code may be used to pre-program and change the daily distraction limit (or other parameters). In this example, the person operating the external adjustment device 180 will not be able to distract more than one (1) mm in a day (or more than two mm in a day), and will not have the security code to be able to change this function of the external adjustment device 180. This serves as a useful lockout feature to prevent accidental over-extension of the intramedullary lengthening device 110. The safety feature may monitor, for example, rotational movement of magnets 186 of the external adjustment device 180, described in more detail below, or the safety feature may monitor rotation of the cylindrical magnet 134 in the intramedullary lengthening device 110, via non-invasive sensing means.

Figure 7:
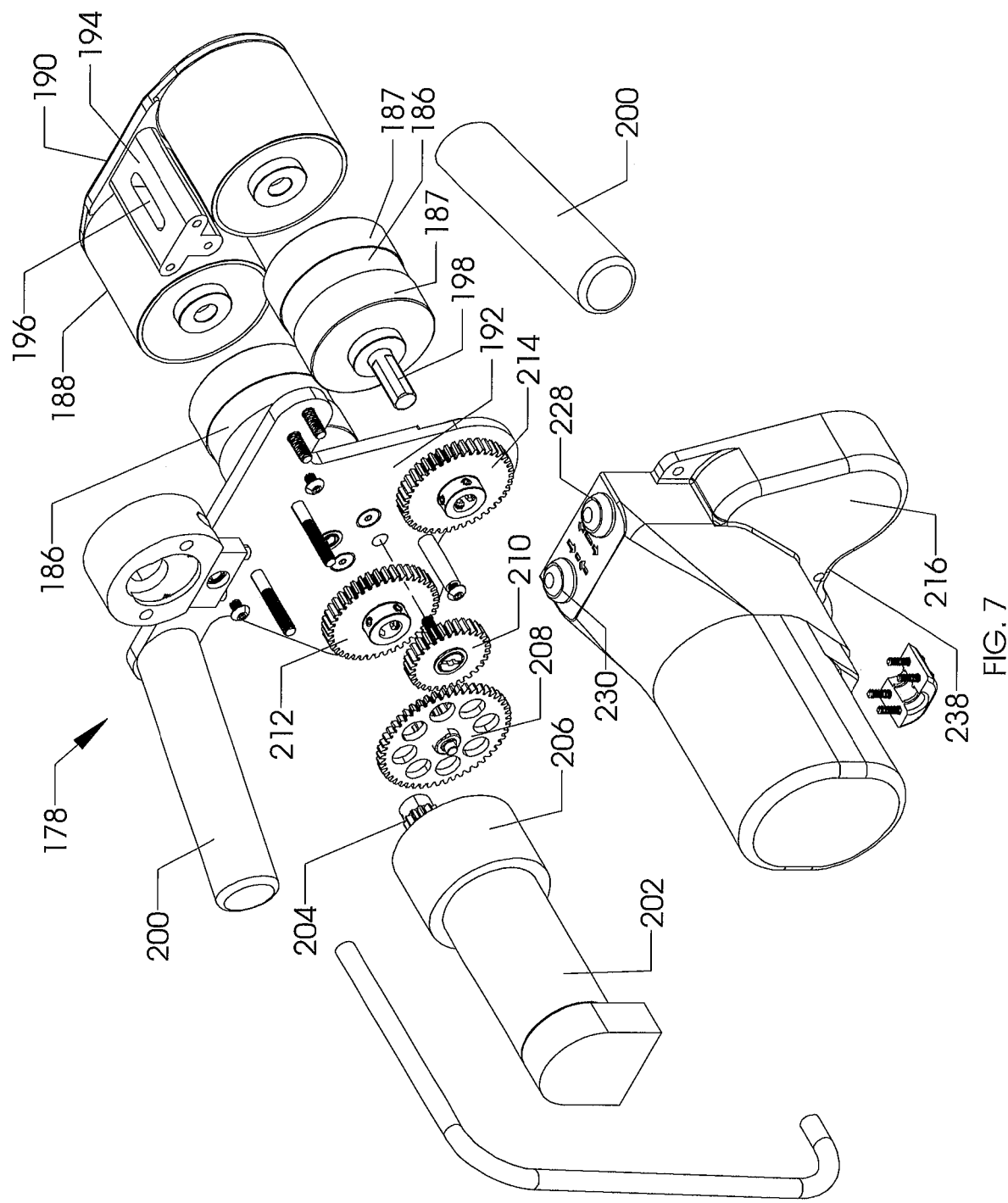
FIG. 7 illustrates an exploded view of the magnetic handpiece of the external adjustment device of FIG. 6.

FIG. 7 shows the detail of the magnetic handpiece 178 of the external adjustment device 180, in order to elucidate the manner that the magnets 186 of the external device serve to cause the cylindrical magnet 134 of the intramedullary lengthening device 110 to turn. As seen in FIG. 7, there are two (2) magnets 186 that have a cylindrical shape. The magnets 186 are made from rare earth magnets. The magnets 186 may have the same radial two pole configuration as the cylindrical magnet 134 seen in FIG. 5. The magnets 186 are bonded or otherwise secured within magnetic cups 187. The magnetic cups 187 include a shaft 198 which is attached to a first magnet gear 212 and a second magnet gear 214, respectively. The orientation of the poles of each the two magnets 186 are maintained in relation to each other by means of the gearing system (by use of center gear 210, which meshes with both first magnet gear 212 and second magnet gear 214). For example, it may be desired that the south pole of one of the magnets 186 is facing up whenever the south pole of the other magnet 186 is facing down. This arrangement, for example, maximizes the torque that can be placed on the cylindrical magnet 134 of the intramedullary lengthening device 110.

The components of the magnetic handpiece 178 are held together between a magnet plate 190 and a front plate 192. Most of the components are protected by a cover 216. The magnets 186 rotate within a static magnet cover 188, so that the magnetic handpiece 178 may be rested directly on the patient, while not imparting any motion to the external surfaces of the patient. Prior to distracting the intramedullary lengthening device 110, the operator places the magnetic handpiece 178 over the patient near the location of the cylindrical magnet 134 as seen in FIG. 9. A magnet standoff 194 that is interposed between the two magnets 186 contains a viewing window 196, to aid in the placement. For instance, a mark made on the patient's skin at the appropriate location with an indelible marker may be viewed through the viewing window 196. To perform a distraction, the operator holds the magnetic handpiece 178 by its handles 200 and depresses a distract switch 228, causing motor 202 to drive in a first direction. The motor 202 has a gear box 206 which causes the rotational speed of an output gear 204 to be different from the rotational speed of the motor 202 (for example, a slower speed). The output gear 204 then turns a reduction gear 208 which meshes with center gear 210, causing it to turn at a different rotational speed than the reduction gear 208. The center gear 210 meshes with both the first magnet gear 212 and the second magnet gear 214 turning them at a rate which is identical to each other. Depending on the portion of the body where the magnets 186 of the external adjustment device 180 are located, it is desired that this rate be controlled, to minimize the resulting induced current density imparted by magnet 186 and cylindrical magnet 134 though the tissues and fluids of the body. For example a magnet rotational speed of 60 RPM or less is contemplated although other speeds may be used such as 35 RPM or less. At any time, the distraction may be lessened by depressing the retract switch 230. For example, if the patient feels significant pain, or numbness in the area being lengthened.

Figure 8:
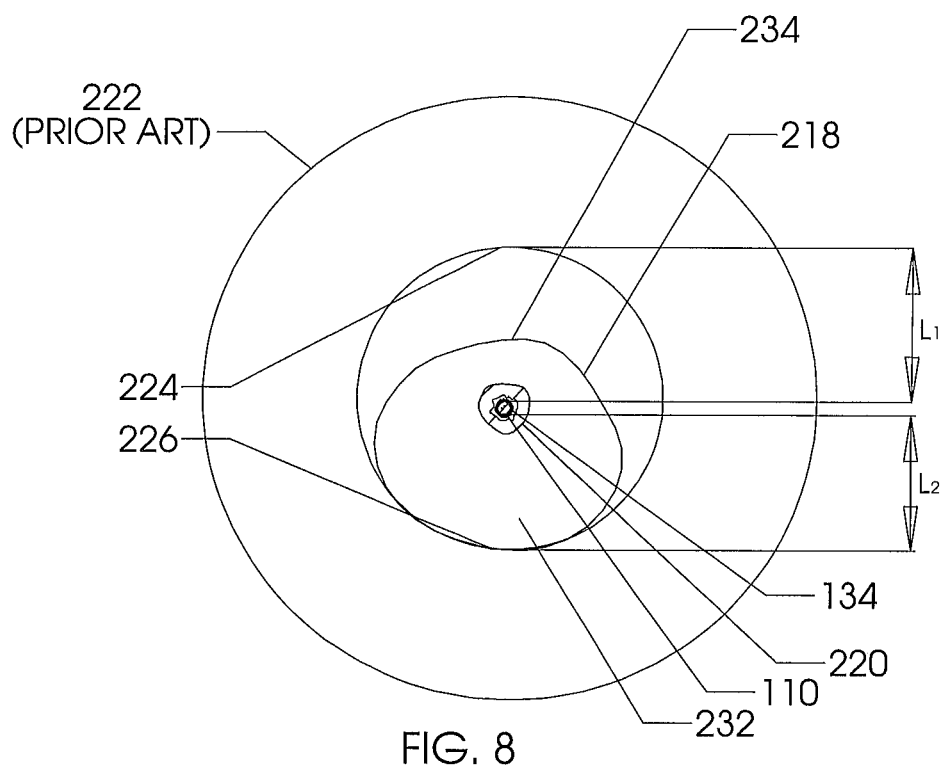
FIG. 8 illustrates a cross-sectional representation of a prior art electromagnetic external device being positioned around a patient's lower thigh.

A cross section of a patient's lower thigh 218 with the intramedullary lengthening device 110 implanted within the femur 220 is shown in FIGS. 8 and 9. In FIG. 9, the magnetic handpiece 178 of the external adjustment device 180 of the invention is shown in position to adjust the cylindrical magnet 134 of the intramedullary lengthening device 110. In FIG. 8, however, a scale depiction of a prior art magnetic stator "donut" 222 demonstrates the comparative efficiency of the two designs (FIG. 8 illustrates an intramedullary lengthening device 110 of the type described herein placed in a "prior art" magnetic stator "donut" 222). The prior art magnetic stator "donut" 222 is large, expensive, and difficult to transport to a patient's home for daily adjustments. In addition, the use of a circular cross-section as a one-size-fits-all device is not very efficient because of several reasons: the cross section of most limbs is not circular, the bone is usually not centered within the limb and patients' limbs come in many different sizes. In FIG. 8, the thigh has been placed through the circular hole in the magnetic stator "donut" and the posterior portion 232 of the thigh rests at the lower portion 226 of the magnetic stator "donut" 222. The strength of a magnetic field decreases in accordance with a power (such as the inverse square) of the distance, depending on the complexity of the specific field geometry. Therefore, in any magnetic design, making the distance between the driving magnetic field and the driven magnet as small as possible is desirable. The size of the patient's lower thigh 218 and the decision to how it is placed within the magnetic stator "donut" 222 in FIG. 8 create a geometry so that the distance $L_1$ between the cylindrical magnet 134 and the upper portion 224 of the magnetic stator "donut" 222 is about the same as the distance $L_2$ between the cylindrical magnet 134 and the lower portion 226 of the magnetic stator "donut" 222. However, if the anterior portion 234 of the thigh were instead placed against the upper portion 224 of the magnetic stator "donut" 222, the length $L_1$ would become less while the length $L_2$ would become greater. Because each patient has a different sized limb, and because small limbs like the upper arm as well as large limbs such as the upper leg are desired for treatment, the magnetic stator "donut" 222 of FIG. 8 is almost impossible to optimize. Therefore, an extra large magnetic field needs to be generated as the standard magnetic field of the device, thus requiring more expense (for the hardware to power this larger field). This in turn means that each patient will be exposed to a larger magnetic field and larger tissue and fluid current density than is really required. It may be desired, in some embodiments, to maintain patient exposure to magnetic fields of 2.0 Tesla or less during operation of the device. It may also be desired, according to another embodiment, to maintain patient exposure of the patient's tissues and fluids to current densities of no more than 0.04 Amperes/meters$^2$ (rms). In addition, because the intramedullary lengthening device 110 is secured to the bone 100, unnecessarily large magnetic fields may cause unwanted motion of the bone 100, for example in any of the radial directions of the cylindrical magnet 134. If the magnetic field is too high, the patient's leg may be moved out of ideal position, and may even cause the patient some annoyance, including pain.

The configuration of the magnetic handpiece 178 of the external adjustment device 180 as shown in FIG. 9 optimizes the ability of the magnets 186 to deliver torque to the cylindrical magnet 134 of the intramedullary lengthening device 110, without exposing the patient to large magnetic fields. This also allows the cylindrical magnet 134 of the intramedullary lengthening device 110 to be designed as small as possible, lowering the implant profile so that it may fit into the humerus, or the tibia and femurs of small stature patients, such as those who might desire cosmetic limb lengthening. As mentioned, a 9 mm diameter intramedullary lengthening device can deliver 100 lb. distraction force, and even 8 mm and 7 mm devices are contemplated. The alternating orientation of the two magnets 186 (i.e., north pole of one magnet 186 corresponding with south pole of the other magnet 186) creates an additive effect of torque delivery to cylindrical magnet 134, and thus maximizes distraction force for any specific cylindrical magnet 134 size. Also, the separation (S) between the centers of the two magnets 186 (for example 70 mm), and the resulting concave contour 238 (FIGS. 6 and 7), match with the curvature of the outer surfaces of the majority of limbs, thus making the distances $L_3$ and $L_4$ between each of the magnets 186 and the cylindrical magnet 134 as small as possible. This is especially aided by the concave contour 238 of the magnetic handpiece 178. Also, skin and fat may be compressed by the magnet covers 188 causing an indentation 236 on one or both sides which allows the distances $L_3$ and $L_4$ between each of the magnets 186 and the cylindrical magnet 134 to be yet smaller.

Figure 10:
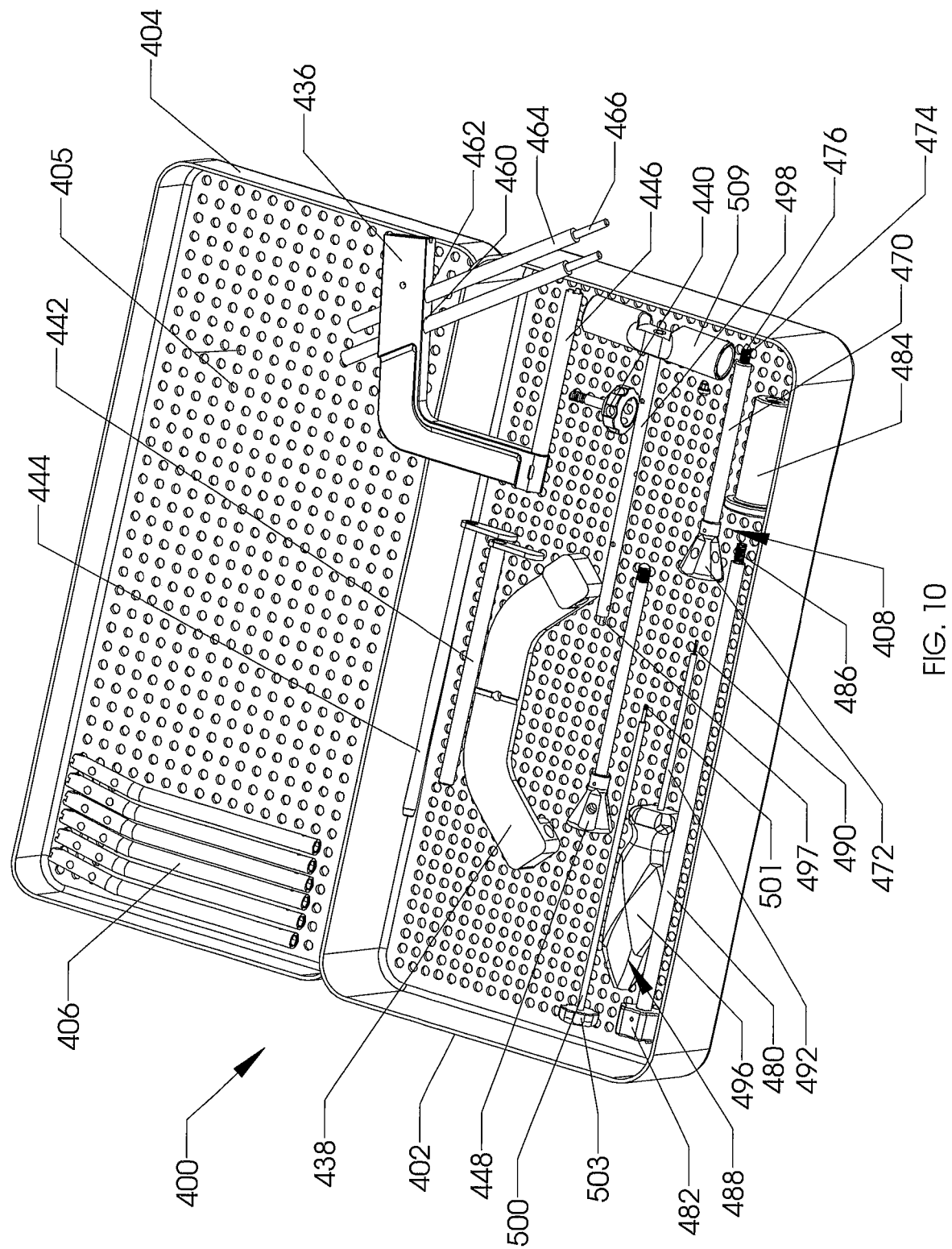
FIG. 10 illustrates a sterilizable kit for use with a modular intramedullary lengthening device.
Figure 11:
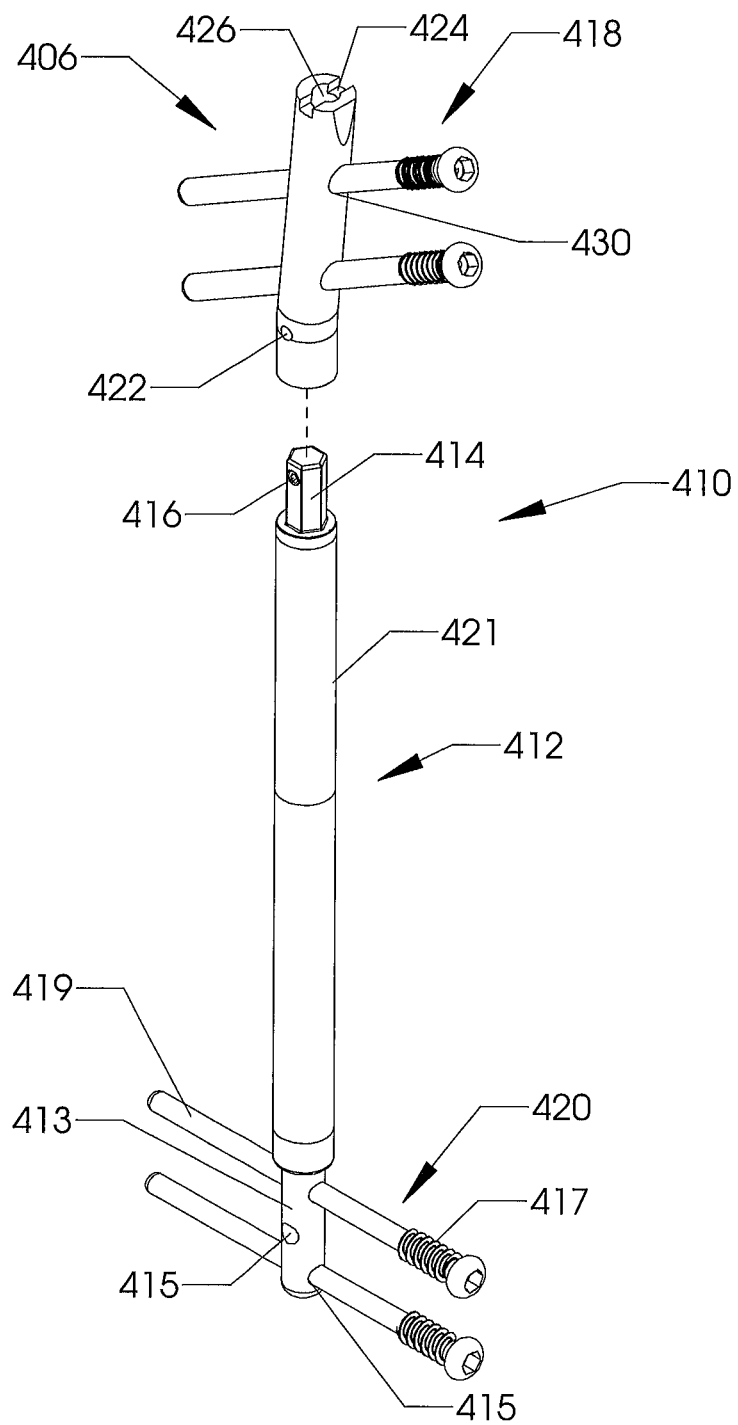
FIG. 11 illustrates a modular intramedullary lengthening device according to one embodiment.

FIG. 10 illustrates a sterilizable kit 400 containing a plurality of extension rods 406 which are configured to be attached to an actuator 412 (FIG. 11) in order to construct a modular intramedullary lengthening device 410 (FIG. 11). In a one embodiment, the actuator 412 is supplied sterile, and the extension rods 406 and the remainder of the contents of the sterilizable kit 400 are sterilizable by autoclave (e.g., steam), Ethylene Oxide or other methods known to those skilled in the art. The sterilizable kit 400 contents includes one or more of the extension rods 406 and accessories 408 for use in the insertion, attachment, adjustment and removal of the modular intramedullary lengthening device 410. The contents are located within a first sterilizable tray 402 and a second sterilizable tray 404. Second sterilizable tray 404 and first sterilizable tray 402 have a plurality of holes 405 to allow gas to enter. Other items in the kit 400 will be described in several of the following figures.

Figure 21A:
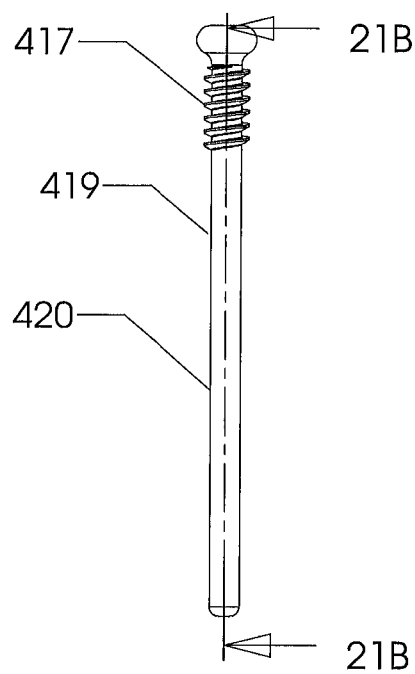
FIG. 21A illustrates a locking screw for use with the intramedullary lengthening device.
Figure 21B:
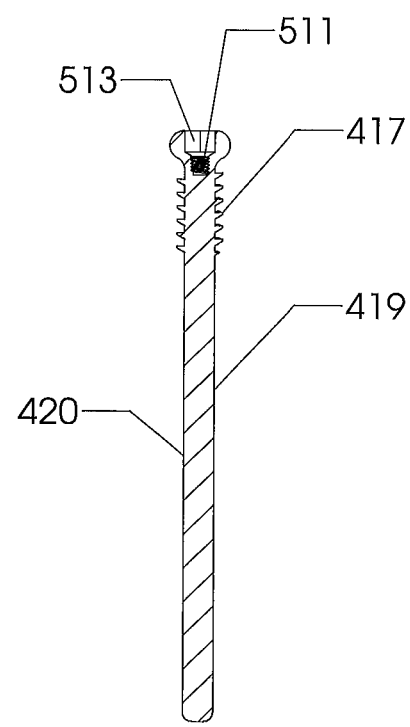
FIG. 21B illustrates the locking screw of FIG. 21A taken along line 21B-21B of FIG. 21A.

Turning to FIG. 11 the assembly of the modular intramedullary lengthening device 410 is shown. The actuator 412 is designed to be placed in the bone of the patient in the opposite orientation than that of the intramedullary lengthening device 110 of FIG. 1. Therefore, the distraction shaft 413 is orientated towards the distal end of the bone (distal is the down direction of FIG. 11). Distal screw holes 415 in the distraction shaft 413 allow the placement of distal locking screws 420. The distal locking screws 420 (FIGS. 21A and 21B) have proximal threads 417 for engaging the bone, while the remainder of the shaft 419 of the distal locking screws 420 is of a constant diameter for maximum strength and stability. At the proximal end 421 of the actuator 412 there is a hexagonally-shaped male hub 414 containing a transverse set screw 416, within a threaded hole 429 of the hexagonal male hub 414 (FIG. 12). The extension rod 406 (FIGS. 13 and 14) has a corresponding hexagonal hole 428 or female end into which the hexagonal male hub 414 of the actuator 412 is placed. The transverse set screw 416 is nested within the threaded hole 429 of the hexagonal male hub 414 so that it does not interfere with the hexagonal hole 428 of the extension rod 406, when they are placed together. There are two set screw holes 422 in the wall of the extension rod 406 which are in line with each other. The actuator 412 and extension rod 406 are placed together so that the set screw holes 422 extend coaxially with the set screw 416. This allows a male hex 490 of a set screw tightening driver, such as the torque limiting driver 488 of FIGS. 10 and 17, to be inserted into a hex hole of the set screw 416. When the torque limiting driver 488 is tightened and ratchets at its set control torque, the other end of the set screw 416, which is either threaded or a non threaded peg, inserts into the opposite set screw hole 422, thus tightly securing the actuator 412 to the extension rod 406. The set screw holes 422 are sized to allow the male hex 490 to smoothly clear, but the non-threaded peg of the set screw 416 clear very slightly, making a static connection that cannot be easily loosened during implantation. If desired, bone cement may be placed in annulus of set screw hole 422, to even further bond set screw 416. Also, a second screw may be screwed in behind the head of the set screw into the female thread that the set screw 416 was originally nested in. The head of this second screw will add additional resistance to shear failure of the set screw 416. In addition, the second screw can be tightened so that it jams into the set screw 416, thus making back-out of the set screw 416 unlikely. Any non-circular cross-section may be used in place of the hex cross-section, for example a square or oval cross-section.

Proximal locking screws 418 insert through locking screw holes 430 in the extension rod 406. The extension rod 406 may be straight, or may have a specific curve 432, for example, for matching the proximal end of the femur or tibia. It can be appreciated that the modular arrangement allows the actuator 412 to be attached to one of numerous different models of extension rods 406, having different lengths, curves (including straight), diameters, hole diameters, and angulations. The first sterilization tray 402 may include many of these different extension rods 406, which may be selected as appropriate, and attached to the actuator 412. Because the actuator 412 is supplied sterile, this arrangement is also desirable, as only a single model need be supplied. However, if desired, several models of actuator may exist, for example, different diameters (10.5 mm, 12.0 mm, 9 mm, 7.5 mm) or with different distal screw hole diameters, configurations or angulations. The preferred configuration for a multitude of patients and different bone types and sizes can be available, with a minimum number of sterile actuator models.

Figure 15:
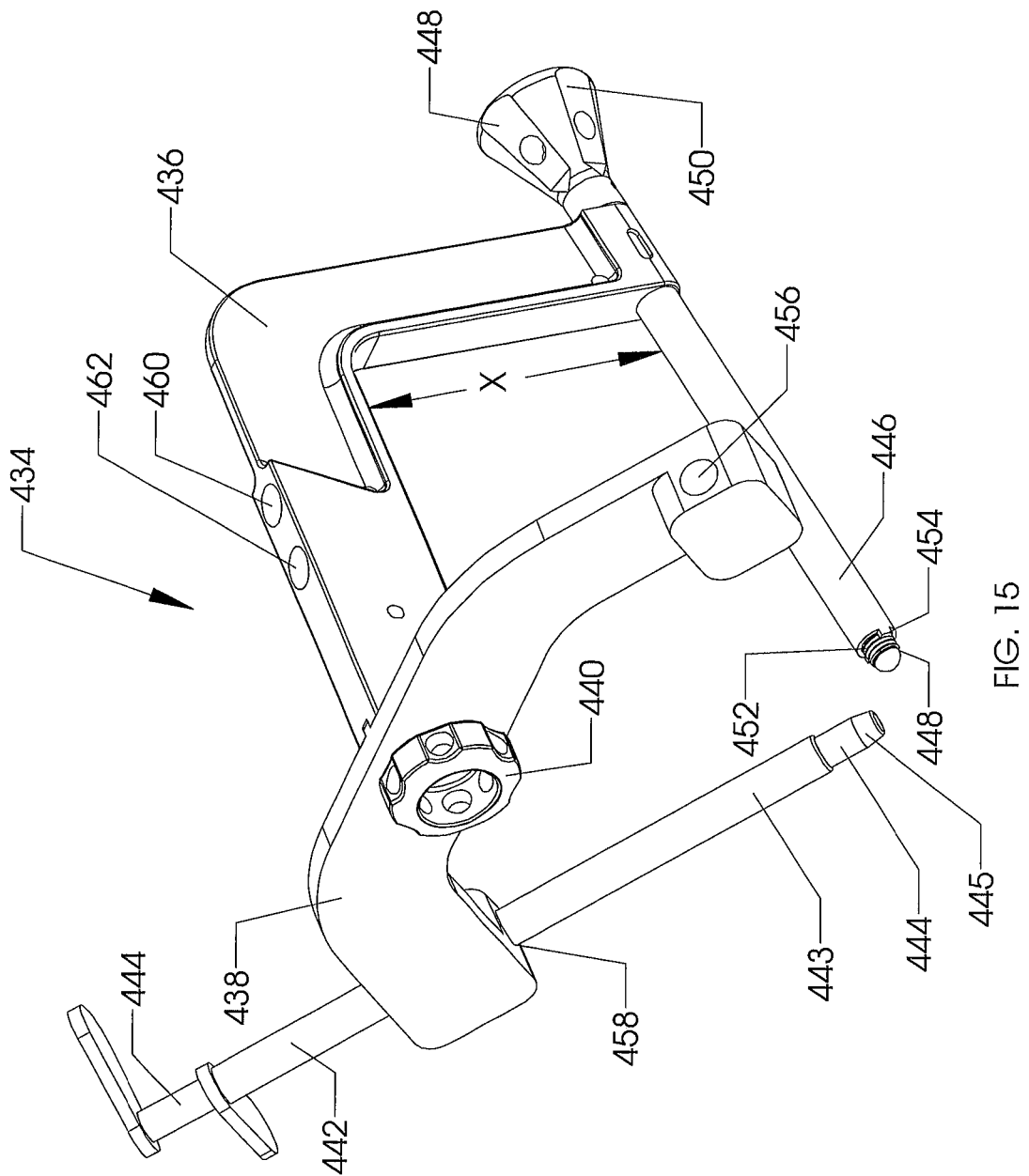
FIG. 15 illustrates a proximal drill guide for insertion and attachment of the modular intramedullary lengthening device.

Turning to FIG. 15, a proximal drill guide 434 is illustrated and is configured for attaching to the modular intramedullary lengthening device 410 to ease its insertion into the intramedullary canal, the drilling of holes in the bone and the attachment of the proximal locking screws 418 to the bone. The proximal drill guide 434 comprises an extension arm 436 attached to a connection tube 446 through which a locking rod 448 is inserted. The locking rod 448 has a locking knob 450 at the proximal end and a male thread 452 at the distal end. In order to temporarily attach the proximal drill guide 434 to the modular intramedullary lengthening device 410, a locking tab 454 of the proximal drill guide 434 is inserted into a locking groove 424 of the extension rod 406 and the locking knob 450 is turned, threading the male thread 452 of the locking rod 448 into a female thread 426 of the extension rod 406. Prior to the procedure a drill guide extension 438 is attached via a knob 440 to the extension arm 436. After reaming the medullary canal of the bone to a diameter slightly larger than the outer diameter of the modular intramedullary lengthening device 410 (for example 11 mm), distal end of the modular intramedually lengthening device 410 is inserted into the medullary canal and the flat proximal surface of the locking knob 450 is hammered with a mallet, allowing the modular intramedullary lengthening device 410 to be inserted to the correct depth. Dimension X is sufficient to clear large thighs or hips (in the worst case femoral application). For example, 8 to 10 cm is appropriate. Once the modular intramedullary lengthening device 410 is in place in the medullary canal, the proximal drill guide 434 is left attached and a guide sleeve 442 is placed through one of the holes 456, 458, 460, 462 and slid so that the distal end 443 reaches the skin of the patient. The drill guide extension 438, extension arm 436 and holes 456, 458, 460, 462 are dimensioned and oriented so that the guide sleeve 442 is oriented at the exact angle to allow drilling and placement of screws through the locking screws holes 430 of the extension rod 406 and through the bone. The skin of the patient is cut and a drill bushing 444 is placed through the incision, with the tapered tip 445 passing through tissue and reaching the bone to be drilled. For example, drills and locking screws may be inserted down the drill bushing 444, or alternatively, drills may be inserted down the drill bushing 444 and then, after the drilling is complete, the drill bushing 444 is removed and proximal locking screw 418 is inserted down the guide sleeve 442. Alternative guide sleeves 464 and drill bushings 466 can be placed through holes 460 and 462, as seen in FIG. 10.

Figure 16:
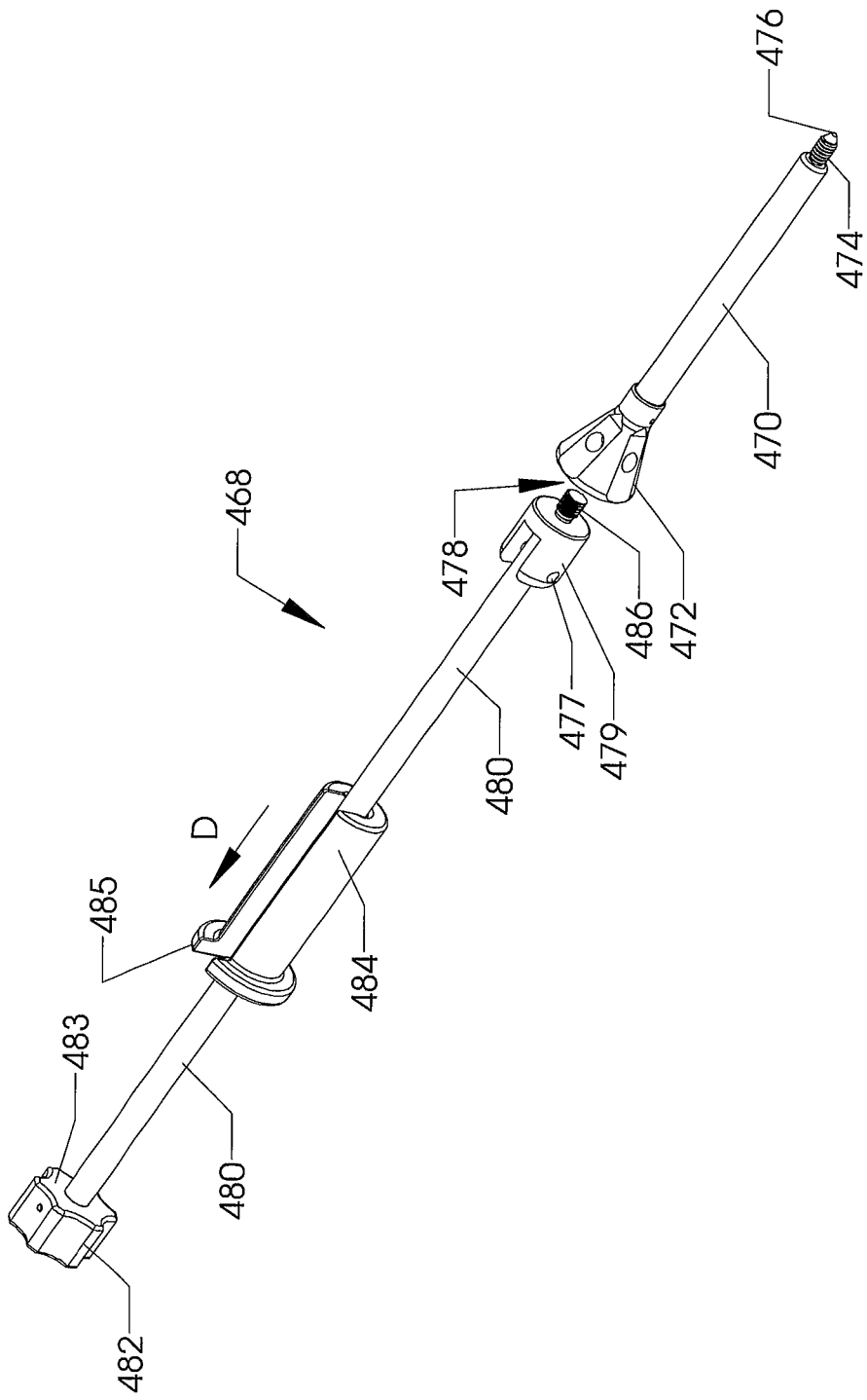
FIG. 16 illustrates a removal tool for removal of the modular intramedullary lengthening device.
Figure 20:
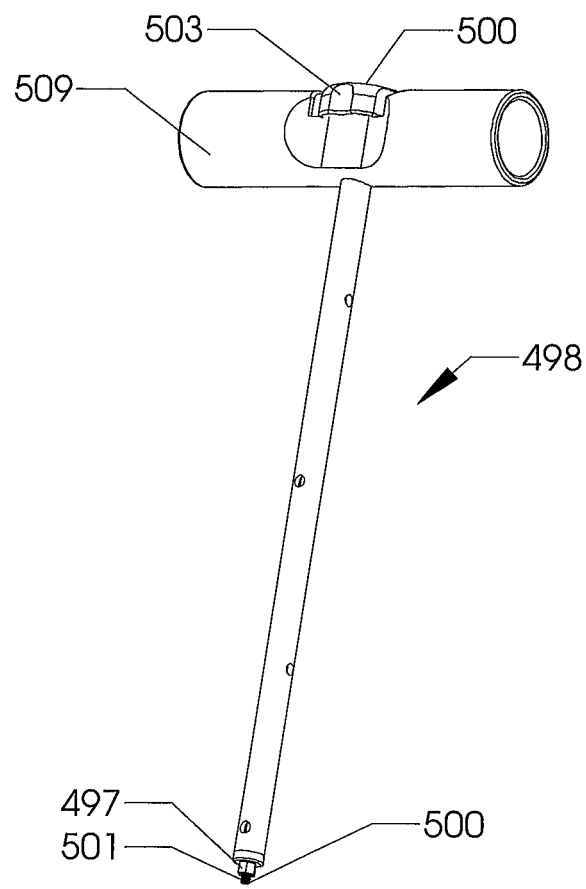
FIG. 20 illustrates a locking screw driver for use with the intrameduallary lengthening device.

Turning to FIG. 16, a removal tool 468 is illustrated. The removal tool 468 is used after the distraction period and consolidation period are complete. To remove the modular intramedullary lengthening device 410 from the medullary canal, the skin is incised and bone exposed at the locations of the proximal and distal locking screws 418, 420 and at the proximal end of the modular intramedullary lengthening device 410. A removal rod 470 is connected to the female thread 426 of the extension rod 406 of the modular intramedullary lengthening device 410 by inserting the engagement tip 476 and screwing the male thread 474 into the female thread 426, holding onto the locking knob 472. The locking knob 472 contains a female thread 478 which allows the attachment of a male thread 486 of a removal extension 480, which has an impact knob 482 and removal hammer 484. The male thread 486 is coupled to the removal extension 480 by a pivot 477 of a pivoting base 479. The male thread 486 is secured to the female thread 478 by grasping and turning the impact knob 482. Prior to removing the modular intramedullary lengthening device 410, the proximal and distal locking screws 418, 420 are removed. They may be removed with the use of the locking screw driver 498 (FIGS. 10 and 20), which has a male hex tip 497 to engage the proximal ends of the locking screws 418, 420. A screw capture rod 500 (FIGS. 10 and 20) inserts down the center of the locking screw driver 498 and has a male threaded tip 501. At a deeper portion past the female hex 513 in the locking screws 418, 420 (FIGS. 21A and 21B) is a female thread 511. The male threaded tip 501 of the screw capture rod 500 threads into the female thread 511 of the locking screws 418, 420, and tightened by using the tightening handle 503 of the screw capture rod 500 which sits at the handle end 509 of the locking screw driver 498 so that once the locking screws 418, 420 are removed from the bone, they are still secured to the locking screw driver 498, and will not become prematurely displaced. For example, the locking screws 418, 420 will not be lost or dropped into the patient. The modular intramedullary lengthening device 410 may now be removed from the medullary canal by grasping the removal hammer 484, and moving it quickly in the direction (D) so that hammer impact surface 485 strikes knob impact surface 483. This is done until the modular intramedullary lengthening device 410 is completely removed. It should be noted that locking knob 450 of the proximal drill guide 434 of FIG. 15 also has a female thread (not pictured) so that during the insertion of the modular intramedullary lengthening device 410, if it is desired to remove the device for any reason, the male thread 486 of the removal tool 468 may be attached to the female thread of the locking knob 450, and the removal hammer 484 can be used against the impact knob 482 to remove the modular intramedullary lengthening device 410.

Figure 17:
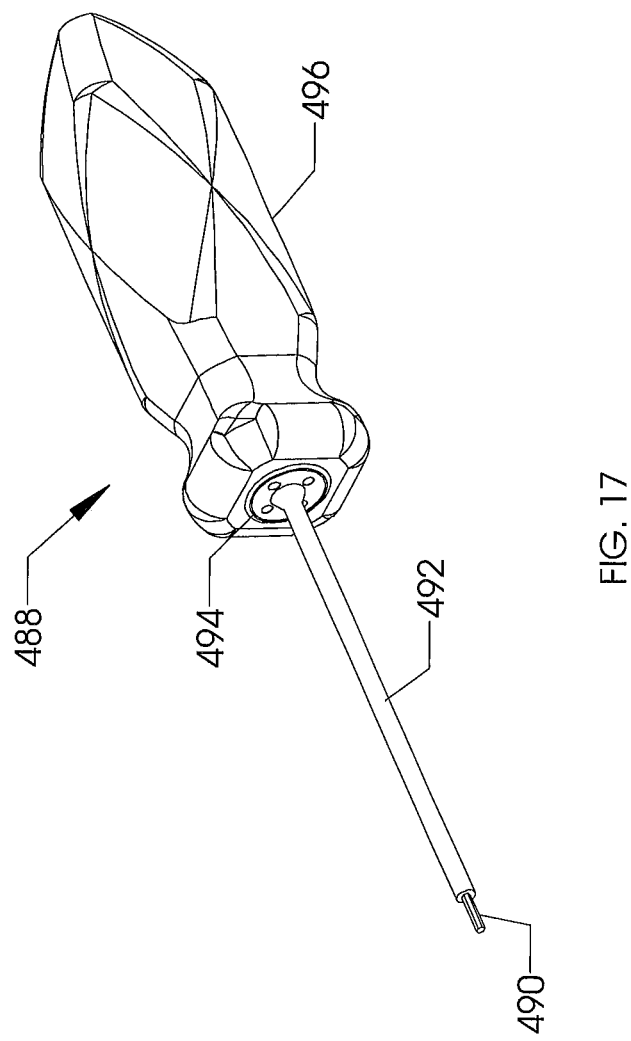
FIG. 17 illustrates a torque limiting driver for attaching the extension rod to the actuator of the modular intramedullary device.

The torque limiting driver 488 of FIG. 17 comprises a handle 496 and a shaft 492 having a torque-specific ratchet 494 connecting them. The male hex tip 490, fits into the hex hole of the set screw 416, or even into the female hex 513 of the locking screws 418, 420. An exemplary ratcheting torque for the set screw 416 is 9 inch-pounds (1.0 Newton-meter), and an exemplary hex size is 1/16" (1.59 mm).

Figure 18:
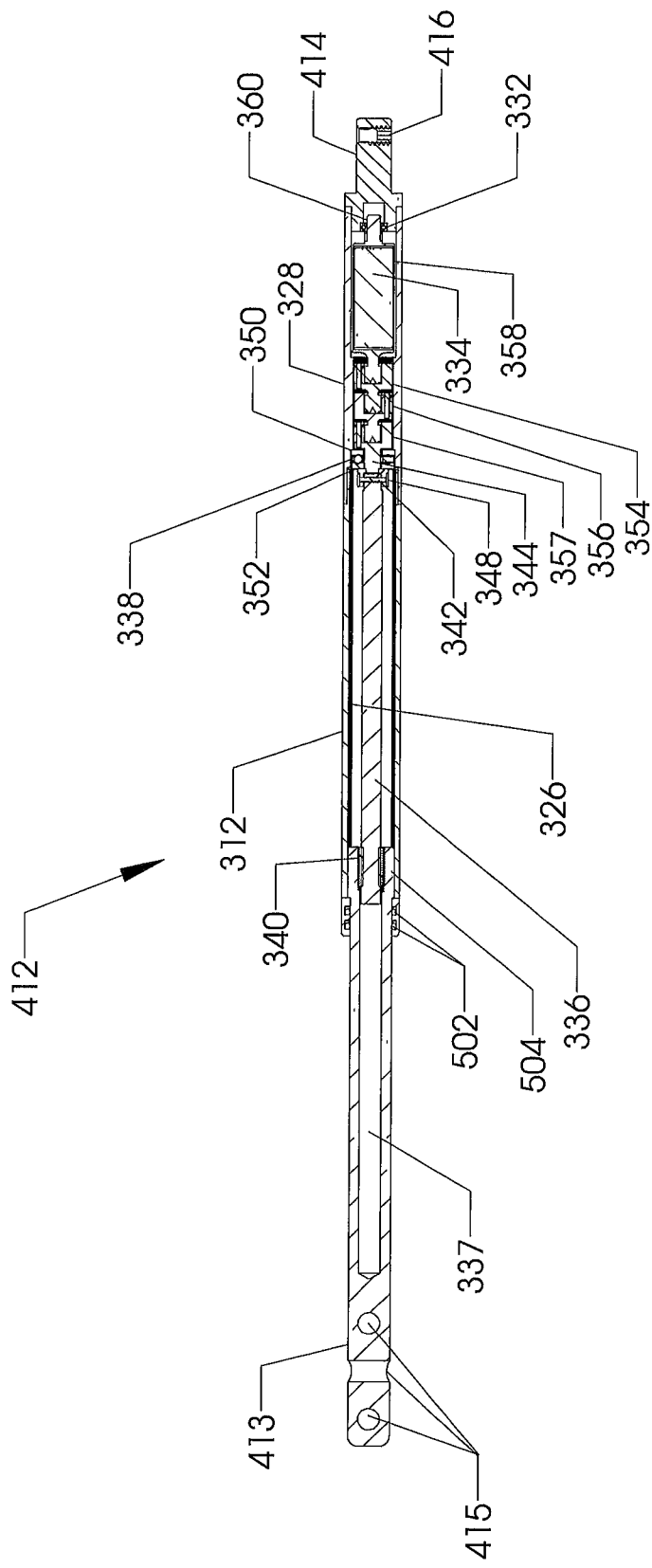
FIG. 18 illustrates a section of the actuator of the modular intramedullary lengthening device.

FIG. 18 illustrates the actuator 412 of FIG. 11 in a sectional view. The distal screw holes 415 are visible in the distraction shaft 413. The distraction shaft 413 is shown in a fully extended position in relation to the housing 312. The cavity 337 has opened to its maximum length. In this embodiment, the distraction shaft 413 has a purely cylindrical surface, and is dynamically sealed to the housing 312 by two o-ring seals 502. The o-ring seals 502 may be made of silicone, EPDM, or other rubber materials, and may be coated with silicone oil, to aid in lubricity. There are four axially extending grooves 326 on the inner wall of the housing 312. Tabs 504 on the end of the distraction shaft 413 fit into these grooves 326 to keep the distraction shaft 413 from being able to rotate with respect to the housing 312. The housing 312 is welded to a magnet housing 328 and the magnet housing 328 is welded to hexagonal male hub 414. The set screw 416 on the hexagonal male hub 414 is used to attach the actuator 412 to the extension rod 406. The cylindrical permanent magnet 334 is cased with epoxy inside magnet casing 358 having an end pin 360. The end pin 360 inserts through radial bearing 332, allowing it to rotate with low friction. As the magnet 334 is rotated by the external magnets, first planetary gear set 354, second planetary gear set 356 and third planetary gear set 357 allow a total reduction of 64:1 (4×4×4). Each gear set allows a 4:1 reduction. Planetary gear output shaft 344 is attached to lead screw 336 by locking pin 342, and locking pin 342 is held in place by cylindrical locking pin retainer 348. Thrust bearing 338 abuts housing abutment or lip 352 and magnet housing abutment or lip 350 (thrust bearing 338 is sandwiched between housing abutment or lip 352 and magnet housing abutment or lip 350). Therefore, thrust bearing 338 abuts housing abutment or lip 352 in tension and magnet housing abutment or lip 350 in compression. It should be noted that the sandwich arrangement allows for some slop or play between the thrust bearing 338 and the housing abutment or lip 352 and the magnet housing abutment or lip 350. Lead screw 336 engages with nut 340, which is secured within distraction shaft 413. With the 64:1 gear reduction of this embodiment, distraction forces of greater than 300 pounds (1334 Newtons) have been consistently achieved with a gap (G in FIG. 19) of 2 inches (5.08 cm) between the magnetic hand piece 178 and the intramedullary lengthening device 110. This is sufficient for distracting a large range of typical patients.

It should be noted that although the embodiments of the intramedullary lengthening devices presented are shown to be used in a preferred orientation (distal vs. proximal), any of these embodiments may be used with the distraction shaft pointing distally or proximally. In addition, the invention may also be applied to distractable bone plates that are not located within the intramedullary canal, but are external to the bone.

An alternative lengthening scheme than those presented above may be also used. For example, one alternative includes the purposeful over-lengthening (to further stimulate growth) followed by some retraction (to minimize pain). For instance, each of four daily 0.25 mm lengthening periods may consist of 0.35 mm of lengthening, followed by 0.10 mm of retraction.

The materials of the accessories 408 are medical grade stainless steel, though other materials of varying densities may be used depending on the desired weight and the required size. The majority of the components of the intramedullary lengthening devices are preferably Titanium or Titanium alloys although some of the internal components may be made from stainless steel.

While embodiments of the present invention have been shown and described, various modifications may be made without departing from the scope of the present invention. As one example, the devices described herein may be used to lengthen or reform a number of other bones such as the mandible or the cranium. The invention, therefore, should not be limited, except to the following claims, and their equivalents.

The invention claimed is:

1. A lengthening device comprising:
a housing configured to be attached relative to a first bone section, the housing having a first abutment and a second abutment about an inner surface of the housing;
a distraction shaft having a cavity along a length thereof and being configured to be attached relative to a second bone section and being telescopically displaceable relative to the housing; and
an actuator configured to increase at least one of a distraction force between the distraction shaft and the housing and a length of the lengthening device, the actuator including:
a permanent magnet being configured for rotation relative to the housing;
a lead screw operatively coupled to the permanent magnet via a gear assembly; and
a thrust bearing disposed about a portion of the gear assembly, the thrust bearing being positioned between the first abutment and the second abutment of the inner surface of the housing.

2. The lengthening device of claim 1, wherein rotation of the permanent magnet causes the actuator to increase at least one of a distraction force between the distraction shaft and the housing and a length of the lengthening device.

3. The lengthening device of claim 1, wherein the gear assembly includes at least one gear operatively connected between the permanent magnet and the lead screw.

4. The lengthening device of claim 1, wherein the gear assembly includes a plurality of intervening gears disposed between the permanent magnet and the lead screw.

5. The lengthening device of claim 1, wherein the thrust bearing abuts at least one of the first abutment and the second abutment in the housing.

6. The lengthening device of claim 1, wherein the thrust bearing is configured to protect at least part of the actuator from compressive or tensile stresses.

7. The lengthening device of claim 3, wherein the thrust bearing is configured to protect at least one of the permanent magnet and the at least one gear from compressive or tensile stresses.

8. The lengthening device of claim 1, wherein the lead screw interfaces with a threaded portion of the cavity.

9. A lengthening device configured for placement inside an intramedullary canal of a bone having first and second separate sections comprising:
a housing configured for attachment to one of the first and second separate bone sections, the housing having a first abutment and a second abutment about an inner surface of the housing;
a distraction shaft having an internal cavity along a length thereof and configured for attachment to the other of the first and second separate bone sections;
a permanent magnet disposed in the housing and configured for rotation;
an output shaft operatively coupled to a lead screw, the lead screw interfacing with a threaded portion of the internal cavity of the distraction shaft;
a gear assembly operatively connecting the permanent magnet and the output shaft; and a thrust bearing disposed about a portion of the gear assembly and thrust bearing being positioned between the first abutment and the second abutment of the inner surface of the housing.

10. The lengthening device of claim 9, wherein the gear assembly comprises at least one planetary gear set comprising a plurality of planetary gears.

11. The lengthening device of claim 10, wherein the gear assembly comprises a first planetary gear set comprising a plurality of planetary gears and a last planetary gear set comprising a plurality of planetary gears, wherein rotation of the permanent magnet turns a sun gear of the first planetary gear set and an output of the last planetary gear set is operatively connected to the output shaft.

12. The lengthening device of claim 9, wherein the thrust bearing abuts at least one of the first abutment and the second abutment in the housing.

13. The lengthening device of claim 9, wherein the thrust bearing is configured to protect at least part of the actuator from compressive or tensile stresses.

14. A lengthening device comprising:
a housing configured to be attached relative to a first location on a bone, the housing having a first abutment and a second abutment about an inner surface of the housing;
a distraction shaft movable relative to the housing and configured to be attached relative to a second location on the bone;
a drive system comprising:
a permanent magnet configured for rotation relative to the housing; and
an output shaft operatively coupled to the permanent magnet via a gear assembly, wherein rotation of the permanent magnet causes movement of the output shaft; and
a thrust bearing disposed in the housing about a portion of the gear assembly between the first abutment and the second abutment of the inner surface of the housing, the thrust bearing configured to protect at least part of the drive system from compressive or tensile stresses.

15. The lengthening device of claim 14, wherein the drive system further comprises at least one gear operatively coupled to the permanent magnet and the output shaft.

16. The lengthening device of claim 14, wherein the at least one gear comprises at least one planetary gear set comprising a plurality of planetary gears, wherein the permanent magnet is operatively connected to a sun gear and the at least one planetary gear set is operatively connected to the output shaft.

* * * * *